(12) United States Patent
Lo et al.

(10) Patent No.: US 7,641,986 B2
(45) Date of Patent: *Jan. 5, 2010

(54) PHOSPHORESCENT DENDRIMERS FOR USE IN LIGHT-EMITTING DEVICES

(75) Inventors: Shih-Chun Lo, Oxford (GB); Paul Leslie Burn, Oxford (GB); Ifor David William Samuel, Fife (GB); Thomas Dimitrios Anthopoulos, Fife (GB)

(73) Assignees: Isis Innovation Limited, Oxford (GB); The University Court Of The University Of St. Andrews, Fife (GB)

( * ) Notice: Subject to any disclaimer, the term of this patent is extended or adjusted under 35 U.S.C. 154(b) by 582 days.

This patent is subject to a terminal disclaimer.

(21) Appl. No.: 10/508,061

(22) PCT Filed: Mar. 18, 2003

(86) PCT No.: PCT/GB03/01132

§ 371 (c)(1),
(2), (4) Date: Feb. 7, 2005

(87) PCT Pub. No.: WO03/079736

PCT Pub. Date: Sep. 25, 2003

(65) Prior Publication Data

US 2005/0116622 A1 Jun. 2, 2005

(30) Foreign Application Priority Data

Mar. 18, 2002 (GB) .................. 0206356.8
Aug. 29, 2002 (GB) .................. 0220091.3
Aug. 29, 2002 (GB) .................. 0220092.1

(51) Int. Cl.
*H01L 51/54* (2006.01)
*C09K 11/06* (2006.01)

(52) U.S. Cl. .............. 428/690; 428/917; 313/504; 313/506; 257/40; 546/4; 546/6; 548/101; 548/402; 136/263

(58) Field of Classification Search ............. 428/690, 428/917; 313/504, 506; 257/40, E51.044
See application file for complete search history.

(56) References Cited

U.S. PATENT DOCUMENTS 6,565,992 B1 * 5/2003 Manners et al. ............. 428/690

(Continued)

FOREIGN PATENT DOCUMENTS

WO    WO 93/12073    6/1993

(Continued)

OTHER PUBLICATIONS

Bodige et al. First-Generation Chiral Metallodendrimers: Stereoselective Synthesis of Rigid D3-Symmetric Tetranuclear Ruthenium Complexes. J. Am. Chem. Soc. 1997, vol. 119, pp. 10364-10369.*

(Continued)

*Primary Examiner*—D. L awrence Tarazano
*Assistant Examiner*—Michael Wilson
(74) *Attorney, Agent, or Firm*—Quarles & Brady LLP

(57) ABSTRACT

A light emitting device having at least one layer that contains a phosphorescent organometallic dendrimer with a metal cation and two or more coordinating groups as part of its core and wherein at least two of said coordinating groups each have a dendron attached, at least one of which dendrons comprises at least one nitrogen atom which forms a part of an aromatic ring system or is directly bonded to at least two aromatic groups.

31 Claims, 11 Drawing Sheets

U.S. PATENT DOCUMENTS

| | | | |
|---|---|---|---|
| 2001/0019782 | A1 | 9/2001 | Igarashi et al. |
| 2002/0102413 | A1* | 8/2002 | Han et al. .................. 428/446 |
| 2003/0068525 | A1* | 4/2003 | Bellmann et al. ........... 428/690 |

FOREIGN PATENT DOCUMENTS

| | | |
|---|---|---|
| WO | WO95/02008 | 1/1995 |
| WO | WO 97/23514 | 7/1997 |
| WO | WO 99/21935 | 5/1999 |
| WO | WO 99/48898 | 9/1999 |
| WO | WO 01/59030 | 8/2001 |
| WO | WO 02/066552 | 9/2002 |
| WO | WO 02/081488 | 10/2002 |

OTHER PUBLICATIONS

Kimura et al. "Energy transfer within rutheniumcored rigid metallodendrimers." Tet. Lett. 2000. vol. 41 pp. 6809-6813.*

Newkome et al. "Suprasupermolecules with novel properties: metallodendrimers." Chem Rev. 1999. vol. 99, pp. 1689-1746.*

GB search report for priority document, Nov. 1923, GB 0206356.

GB search report for priority document, Aug. 1924, GB 0220091.

GB search report for priority document, Aug. 1924, GB 0220092.

H. Xie et al., Reduction Of Self-Quenching Effect In Organic Electrophosphorescence Emitting Devices . . . , 13 Adv. Mater. 1245-1248 (2001).

M. Ikai et al., Highly Efficient Phosphorescence From Organic Light-Emitting Devices With An Exciton-Bloc Layer, 79 Applied Physics Letters 156-158 (2001).

M. Sluis et al., Synthesis Of Novel Phosphaalkene-Based Bidentate Ligands . . . , 18 Organometallics 1402-1407 (1999).

M. Gutierrez et al., Cyclometallation. Palladium 2-arylpyridine Complexes, 202 J. Organometallic Chem. 341-350 (1980).

X. Gong et al., Trifunctional Light-Emitting Molecules Based on Rhenium And Ruthenium Bipyridine Complexes, 10 Adv. Mater. 1337-1340 (1998).

A. Freeman et al., Dendrimer-Containing Light-Emitting Diodes: Toward Site-Isolation Of Chromophores, 122 J. Am. Chem. Soc. 12385-12386 (2000).

Z. Zhu et al., Synthesis And Characterization Of Monodendrons Based On 9-Phenylcarbazole, 65 J. Org. Chem. 116-123 (2000).

M. Baldo et al., Highly Efficient Phosphorescent Emission From Organic Electroluminescent Devices, 395 Nature 151-154 (1998).

V. Cleave et al., Harvesting Singlet And Triplet Energy In Polymer LEDs, 11 Adv. Mater. 285-288 (1999).

D. O'Brien et al., Electrophosphoresence From A Doped Polymer Light Emitting Diode, 116 Synthetic Metals 379-383 (2001).

S. Lamansky et al., Highly Phosphorescent Bis-Cyclometalated Iridium Complexes: Synthesis, Photophysical Characterization, And Use In Organic Light Emitting Diodes, 123 J. Am. Chem. Soc. 4304-4312 (2001).

S. Lamansky et al., Synthesis And Characterization Of Phosphorescent Cyclometalated iridium Complexes, 40 Inorg. Chem. 1704-1711(2001).

C. Adachi et al., Endothermic Energy Transfer: A Mechanism For Generating Very Efficient High-Energy Phosphorescent Emission In Organic Materials, 79 Applied Physics Letters 2082-2084 (2001).

M. Baldo, Very High-Efficiency Green Organic Light-Emitting Devices Based on Electrophosphorescence, 75 Applied Physics Letters 4-6 (1999).

J. Lupton et al., Control Of Electrophosphorescence . . . 11 Adv. Funct. Mater. 287-294 (2001).

M. Kawa et al., Enhanced Luminescence Of . . . 331Thin Solid Films 259-263 (1998).

Abstract of JP 2003-231692 published Aug. 19, 2003.

Machine translation of JP 2003-231691 published Aug. 19, 2003.

Issberner et al., Angew. Chem. Int. Ed. Engl. (1994) 33: 23/24, 2413-2420.

* cited by examiner

D = Dendron

PHOSPHORESCENT DENDRIMERS FOR USE IN LIGHT-EMITTING DEVICES

This application claims priority on GB0206356.8 filed on Mar. 18, 2002, GB0220091.3 filed on Aug. 29, 2002, GB0220092.1 filed on Aug. 29, 2002, and PCT/GB03/01132 filed on Mar. 18, 2003.

This invention relates to metal-containing phosphorescent dendrimers with at least one dendron that comprises one or more units that contain a nitrogen atom and light-emitting devices containing them.

A wide range of luminescent low molecular weight metal complexes are known and have been demonstrated as both light emitting and charge transporting materials in light emitting devices, in particular light-emitting diodes (LEDs) also known as electroluminscent (EL) devices. To make efficient devices there must be good charge injection, transport and emission from the excitonic state formed. For fluorescent molecules, a simple analysis of spin statistics associated with the injection of oppositely charged carriers which pair to form excitons shows that only 25% of the excitons formed in the LED are in the singlet state with the remainder forming triplets assuming 100% capture of the charged species. However it has been suggested that the barrier of 25% for singlet excitons may be exceeded for fluorescent polymers but it is still known to be far from 100%. For most organic materials only the singlet states can decay radiatively generating light, the triplet states decay non-radiatively. The possibility to extract luminescence from the triplet excited state has recently been demonstrated by inclusion of phosphorescent guest metallic complexes in host matrices. These phosphorescent metal complexes are generally used in a blend with an organic host. The organic host plays an important role as it is involved in charge transport but also acts as a triplet source, i.e. it transfers the excited state to the metal complex for emission. The main type of hosts used are based on carbazoles, e.g., CBP (4,4'-N,N'-dicarbazole-biphenyl) (H.Z/Xie et al, Adv. Mater., 2001, 13, 1245) and TCTA (4,4',4''-tris-(carbazol-9-yl) triphenylamine) (M. Ikai et al, Appl. Phys. Lett., 2001, 79, 156). It should also be noted that TCTA contains a triarylamine moiety and it has been shown that this can be advantageous. However, at times blend systems are sensitive to the concentration of the guest in the host and only low concentrations of the guest can be used before phase separation leads to aggregation or intermolecular interactions of the emissive species increases and this leads to emission quenching. It has been demonstrated that for optimum emission the proportion of phosphorescent emitter to host needs to be low to avoid triplet-triplet annihilation.

In addition the metal complexes used to date have been designed to be volatile so that layers can be deposited by thermal evaporation. For OLEDs using evaporated emitting layers the guest and host are co-evaporated, but this is a difficult process to control accurately, that is to get the correct ratio of guest to host. Co-evaporated layers may also lead to the greater probability of having two phosphorescent emitters closer together than in layers deposited from spin-coating a homogeneous solution of the two components. In many applications solution processing would be preferable to evaporation, but the current molecular materials do not form good films when deposited by solution processing. In addition it would be advantageous to have guest host systems in which high levels of guest can be used. This is possible with dendritic materials.

We have already disclosed in British Application No. 0106307.2 that these problems are solved by forming certain dendrimers with metal ions as part of the core. Dendrimers are branched macromolecules in which branched dendrons (also called dendrites) are attached to a core. The properties of the dendrimers make them ideal for solution processing and allow incorporation of metal complex chromophores, which have been demonstrated to be effective in light emitting devices (LEDs), into a solution processable system.

Phosphorescent guest-host emissive layers that are produced by solution processing from a homogeneous solution should have the advantage that the phosphorescent guest is evenly distributed throughout the formed film, assuming of course that there is no phase separation. We have demonstrated that for dendrimers with iridium as part of their core device performance is more tolerant of guest-host composition than evaporated devices containing iridium complexes. We believe that this is due to the more homogeneous films produced and the fact that the dendritic architecture keeps the cores separated and reduces triplet-triplet quenching.

Although the prior application shows how to produce solution processable phosphorescent dendrimers, the most efficient LEDs from the dendrimers disclosed in British Application No. 0106307.2 still require that the dendritic phosphorescent guest is blended with a host material. We have now appreciated, according to the present invention, that it would be advantageous to have material in which the two components of the blend are in a single molecule for the following reasons:

1. It is critical that each time a blended film is prepared the correct ratio of guest to host material is used and this need is obviated if the components are within a single molecule.
2. The dendritic structure can be involved in the transportation of charge.
3. Incorporation of the components in a single molecule can give improved light emission.
4. The single molecule can allow simpler manufacturability.
5. The single molecule can give improved electrochemical stability.
6. Having the two components of the blend incorporated in a single molecule can give improved film stability, i.e. with no tendency for phase separation over time.

Accordingly the present invention provides a light emitting device and, in particular, a light emitting diode, which comprises at least one layer that contains a phosphorescent organometallic dendrimer with a metal cation and two or more coordinating groups as part of its core and wherein at least two of said coordinating groups each have a dendron attached, at least one of which dendrons comprises at least one nitrogen atom which forms part of an aromatic ring system or is directly bonded to at least two aromatic groups, as well as the dendrimers used therein.

Typically, said phosphorescent dendrimer is located between an anode and a cathode.

The dendrimers typically have the formula (I):

CORE-[DENDRON]$_n$     (I)

in which CORE represents a group containing a metal ion, n represents an integer of 2 or more, each DENDRON, which may be the same or different, represents a dendritic molecular structure comprising at least one nitrogen atom which forms part of an aromatic ring system or is directly attached to at least two aromatic groups such that two or more coordinating groups have different DENDRON attached, CORE terminating in the single bond to the first nitrogen atom or aromatic ring to which more than one dendritic chain is attached, said nitrogen atom or ring forming part of said DENDRON. In a preferred embodiment the dendrons are inherently at least partially conjugated.

When the phosphorescent organometallic dendrimer of the invention has the formula (I), the CORE moiety is typically an organometallic moiety. As used herein, an "organometallic" compound or an "organometallic" moiety is a metal-containing compound or moiety. Preferred "organometallic" compounds and "organometallic" moieties are compounds and moieties in which a ligand is attached to a metal via a carbon-metal bond.

In an alternative embodiment the first branching point is an $sp^3$ hybridised carbon atom.

Dendrons are comprised of branching units and, optionally, linking units. The generation of a dendron is defined by the number of sets of branching units in the dendron. In a second generation dendron, there is a first branching unit, and each of the branches stemming from that first branching unit then branches again ("the second branching units"). In a third generation dendron, each of the branches stemming from the second branching units would themselves branch again, and so on for higher generation dendrons. Suitable branching units include aryl and heteroaryl, which can be fused, and N. It should be noted that a N-containing fused heteroaryl ring such as carbazole can be considered a branching point. The links between branching points include bonding combinations such as aryl-aryl, aryl-vinyl-aryl, aryl-acetylenyl-aryl, aryl-aryl'-aryl (where aryl' may be different from aryl), N-aryl and N-aryl'-N where aryl and N are branching units. Preferred linking units include phenyl and fluorenyl. An individual dendron may contain one or more of each type of branching point. Moreover, in the case of the aryl-vinyl-aryl and aryl-acetylenyl-aryl linkages within the dendron there may be one or more aryl-vinyl or aryl-acetylenyl link between the branching points. Indeed there may be more than one vinyl or acetylenyl or aryl moiety between two aryl branching units but preferably no more than three. Further, there can be advantages in using an asymmetric dendrimer i.e. where the dendrons are not all the same.

Typically, at least one dendron is at least second generation.

Inherently at least partially conjugated dendrons (dendrites) indicate that they are made up of alternating double and single bonds or N lone pairs, apart from the surface groups. However this does not mean that the π system is fully delocalised. The delocalisation of the π system is dependent on the regiochemistry of the attachments. In an inherently at least partially conjugated dendron any branching nitrogen will be attached to 3 (hetero)aryl groups. It is preferred that at least one, and especially all, of the dendrons is/are inherently at least partially conjugated.

As used herein the terms aryl, vinyl, acetylenyl etc. refer to such groups that are divalent, trivalent or multivalent as appropriate. In a preferred embodiment, the dendrons are conjugated. In one preferred embodiment, at least one dendron comprises a nitrogen atom which forms part of an aromatic ring system. In another embodiment, at least one dendron is at least second generation and comprises a nitrogen atom which is directly attached to at least two aromatic groups. In one embodiment the core (or CORE) is attached to a nitrogen atom within the dendron which forms part of an aromatic ring system or is attached to two other (hetero) aryl groups. In a preferred embodiment the nitrogen atom forms part of an aromatic ring system, especially a carbazole group or is attached to two aromatic groups, preferably phenyl groups or substituted fluorenyl groups such that the nitrogen atom forms part of a di- or tri-arylamine group. Preferably at least two dendrons possess such a nitrogen-containing aromatic ring system.

Alternatively, the first single bond is attached to an aryl group, preferably a phenyl group. In a preferred embodiment the aryl group is attached to at least one carbazole group. In one embodiment the N-containing units within the dendron are carbazole units. In a preferred embodiment the branching points are carbazole units attached through the N, 3 and 6 positions. In another preferred embodiment the carbazole branching points are directly linked whilst in another they are separated by an aryl group, preferably phenyl. In another embodiment the dendrons have the nitrogen only included in a carbazole moiety, and all the dendrons attached to the core are of this type. It should also be noted that depending on which unit the nitrogen atom is in it can be part of an electron-transport or hole-transport or bipolar moiety. For bipolar properties carbazole units are preferred, for hole-transporting (HT) properties triarylamines are preferred and for electron-transporting (ET) properties either oxadiazole, benzamidazole, quinoxaline or triazole groups are preferred. Thus, typically, the dendron takes the structure

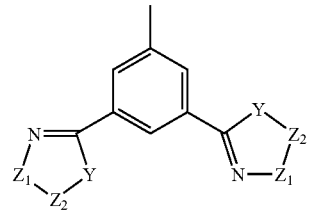

wherein Y is oxygen in which case, —$Z_1$—$Z_2$— represents —N=$CR^1$—, or Y is —N—$R^2$ in which case —$Z_1$—$Z_2$ forms part of a benzene ring or —N=$CR^1$, $R^1$ represents an optionally substituted benzene radical and $R^2$ represents an optionally substituted alkyl or aryl group. Thus the nitrogen-containing rings are either oxadiazoles or imidazoles or triazoles. $R^1$ is typically substituted by one or more surface groups, e.g. 3,5-di-tertiary butyl. $R^2$ is phenyl, which is preferred, or alkyl, for example of 1 to 15 carbon atoms such as methyl or ethyl; these can be substituted, for example when $R^2$ is phenyl then it can be substituted with, for example, one or more alkyl, alkoxy or halo substituents. Specific examples of dendrimers with such a dendron are shown in FIG. 9. It will be appreciated that the dendrons in a dendrimer can contain mixtures of ET, HT and bipolar components, and these are preferably in separate dendrons so that they are not in conjugation with each other.

It is preferred that when the last branching unit in a dendron is a triarylamine then the distal aryl groups possess one or more surface groups that are not hydrogen atoms. It is further preferred in this case that the dendrons are at least inherently partially conjugated.

In particular, DENDRON comprises in part an aromatic unit which contains a nitrogen atom. This nitrogen atom either forms part of an aromatic ring system or is directly attached to two or three aromatic groups. Where the nitrogen is part of a ring system, it is preferably in a carbazole group, and when it is attached to aromatic groups, the aromatic groups are preferably phenyl or substituted fluorenyl or heteroaryl groups.

Typically, the dendrimer comprises a dendron having a plurality of nitrogen atoms. More preferably, said dendron has a plurality of nitrogen atoms, each being part of a carbazole group. Further, all the nitrogen atoms in said dendron are preferably part of carbazole groups.

In a preferred embodiment the dendrimer comprises 3-21 carbazole units.

The present invention also provides a device which comprises at least one layer that contains a phosphorescent organometallic compound with a metal cation and two or more co-ordinating groups as part of its core and wherein at least two of said co-ordinating groups each have a substituent attached, at least one of which substituents comprises at least one nitrogen atom which forms part of an aromatic ring system or is directly bonded to at least two aromatic groups, said nitrogen atom being linked to the coordinating group by a direct bond or an optionally substituted hydrocarbyl group.

Also provided is a phosphorescent organometallic compound with a metal cation and two or more co-ordinating groups as part of its core and wherein at least two of said co-ordinating groups each have a substituent attached, at least one of which substituents comprises at least one nitrogen atom which forms part of an aromatic ring system or is directly bonded to at least two aromatic groups, said nitrogen atom being linked to the co-ordinating group by a direct bond or an optionally substituted hydrocarbyl group.

Typically, said substituent is a carbazole group. Typically, said optionally substituted hydrocarbyl group is a $C_2$-$C_{12}$ hydrocarbyl group. Preferably, said optionally substituted hydrocarbyl group is phenyl or $C_2$-$C_{12}$ alkylene, for example ethylene.

For molecular phosphorescent iridium based materials it has been reported that the host which often contains carbazole units can transfer its energy to the phosphorescent guest for emission. In the case of green and red emission the host has been reported to have higher energy levels than the guest and for blue emission the energy levels of the host are reported to be lower than the guest. In the dendrimers that contain the host components in the dendron, the dendron singlet or triplet energy should preferably be such that it can, if formed, be transferred to the core for emission. Therefore whilst the singlet or triplet energy of the dendrons is normally greater than the emission energy of the core it can be below that of the core providing the energy difference is small enough to allow the transfer of energy to the core. To aid this it is preferred that the triplet excited states of the dendrons must be longer lived than the emissive state of the core.

The dendrimers of the invention are preferably luminescent in the solid state. The luminescent moiety may be partially or wholly within the core itself. The luminescence is preferably from the metal cation containing core.

Suitable surface groups for the dendrimers, which are preferably present, and are attached to the distal (hetero)aryl group include branched and unbranched alkyl, especially t-butyl, branched and unbranched alkoxy, for example 2-ethylhexyloxy, hydroxy, alkylsilane, carboxy, carbalkoxy, and vinyl. A more comprehensive list include a further-reactable alkene, (meth)acrylate, sulphur-containing, or silicon-containing group; sulphonyl group; polyether group; $C_1$-to-$C_{15}$ alkyl (preferably t-butyl) group; amine group; mono-, di- or tri-$C_1$-to-$C_{15}$ alkyl amine group; —COOR group wherein R is hydrogen or $C_1$-to-$C_{15}$ alkyl; —OR group wherein R is hydrogen, aryl, or $C_1$-to-$C_{15}$ alkyl or alkenyl; —O$_2$SR group wherein R is $C_1$-to-$C_{15}$ alkyl or alkenyl; —SR group wherein R is aryl, or $C_1$-to-$C_{15}$ alkyl or alkenyl; —SiR$_3$ group wherein the R groups are the same or different and are hydrogen, $C_1$-to-$C_{15}$ alkyl or alkenyl, or —SR' group (R' is aryl or $C_1$-to-$C_{15}$ alkyl or alkenyl), aryl, or heteroaryl. Typically t-butyl and alkoxy groups are used. Different surface groups may be present on different dendrons or different distal groups of a dendron. In one embodiment, there are surface groups present on the dendron which comprises the N atom which forms part of an aromatic group or is attached to at least two aromatic groups. It is preferred that the dendrimer is solution processable i.e. the surface groups are such that the dendrimer can be dissolved in a solvent.

The surface group can be chosen such that the dendrimer can be processed to the required form, for example a thin film for an OLED. Hence, it will be appreciated that it is preferred that the surface groups are groups which contain at least two carbon atoms, for example $C_2$-$C_{15}$ alkyl or OR where R is aryl or $C_2$-$C_{15}$ alkyl or alkenyl. More preferably, the surface groups will contain 4 or more carbons for example tert-butyl. In addition, the surface group can be chosen such that the dendrimer can be patterned. For example, a cross-linkable group is present which can be cross-linked upon irradiation or by chemical reaction. Alternatively the surface group comprises a protecting group which can be removed to leave a group which can be cross-linked. In general, the surface groups are selected so the dendrimers are soluble in solvents suitable for solution processing.

The aryl groups within the dendrons can be typically benzene, napthalene, biphenyl (in which case an aryl group is present in the link between adjacent branching points) anthracene, fluorene, pyridine, oxadiazole, triazole, triazine, thiophene, carbazole, quinoxaline and where appropriate substituted variations. Typical substituents include C, to $C_{15}$ alkyl or alkoxy groups. The aryl groups at the branching points are preferably benzene rings, preferably coupled at ring positions 1, 3 and 5, triazinyl or carbazole rings. These groups may optionally be substituted. The carbazole units are typically connected at the 3-, 6- and N positions.

It will be appreciated that one or more of the dendrons attached to the core can be unconjugated. Typically such dendrons include ether-type aryl dendrons, for example where benzene rings are connected via a methyleneoxy link. It will also be appreciated that when there is more than one dendron, the dendrons can be of the same or different generation (generation level is determined by the number of sets of branching points). It may be advantageous for at least one dendron to be of the second, or higher, generation to provide the required solution processing properties. Second, or higher, generation dendrons are particularly useful in the cases when the nitrogen atom is attached to aryl groups and the nitrogen atom acts as the branching unit in the dendron, e.g. the nitrogen atom is directly attached to 2 or 3 aryl groups and the dendron containing the nitrogen atom is of second, or higher, generation. When the branching unit is a nitrogen atom, for a given degree of branching, the dendrons are relatively small (that is incorporate a relatively small number of atoms) compared to a dendron in which the branching unit is an aromatic ring incorporating a nitrogen atom (e.g. carbazole). Larger dendrons can improve film forming properties and increase the spacing of the luminescent cores.

The cores typically comprise a metal cation and attached ligands; the metal is central in the core and the core is luminescent. It should be noted that although the core is emissive the attachment of, and the regiochemistry of attachment of, the dendrons can directly affect the emissive properties of the core. The core normally comprises the metal cation and the aryl and heteroaryl units directly attached to the metal. In some cases the heteroaryl and aryl can also form a branching point, e.g. if a second dendron is attached to the aryl or heteroaryl unit that is connected to the metal cation. However in such cases it is still the case that the dendrons attached to the (hetero)aryl unit that is bound to the metal cation must themselves contain at least one nitrogen atom which forms part of an aromatic ring system or is directly bonded to at least two aromatic groups. It is to be understood that the term "metal ion" or "metal cation", as used herein, describes the charge state the metal would have without ligands attached (the oxidation state). In the dendrimers that contain a metal cation the overall charge of the dendrimer is neutral and the metal-ligand bonding will have more or less covalent character depending on the metal and ligand involved.

When the core comprises a metal cation and attached ligands it is typically a complex of a metal cation and two or more coordinating groups, at least two of the coordinating groups being bound to dendrons. Typically the luminescence of the dendrimer will derive from that complex. CORE is typically a complex of a metal cation and two or more coordinating groups, at least one and preferably two or more of the said groups each being bound to a DENDRON moiety as defined in formula (I) by the single bond in which CORE in this formula terminates. It is especially preferred that dendrons, in particular DENDRONS are attached to all of the coordinating groups forming part of the CORE. For example in the iridium dendrimer Examples (5, 7, 25 see below) DENDRONS are attached to all three coordinating groups.

In one aspect of the invention CORE may be represented as a complex of the following formula (II):

  (II)

wherein M is a metal cation, each [X—], which are the same or different, is a coordinating group X attached to a single bond in which CORE terminates, each Y, which may be the same or different, is a coordinating group, q is an integer of 2 or more and r is 0 or an integer, the sum of (a·q)+(b·r) being equal to the number of coordination sites available on M, wherein a is the number of coordination sites on [X—] and b is the number of coordination sites on Y.

The single bond to the branching group may be directly from the co-ordinating group or via an intervening group, typically an ethylene, substituted ethylene, vinylene, substituted vinylene or acetylethyl group.

The single bond in the or each [X—] moiety, being a bond in which CORE terminates, connects to a dendron. Preferably there are at least two dendrons in a dendrimer, in which case q in formula (II) is an integer of 2 or more. The said two or more dendrons typically have the structures represented by DENDRON as defined above. The coordinating groups Y, when present, are neutral or charged chelated ligands which are not attached to dendrons and which serve to fulfil the coordination requirements of the metal cation. Suitable Y include arylpyridines and heteroaryl pyridines and substituted variants. Other alternative Y ligands include β-diketonates, 2-carboxylpyridines, such as picolinic acid, triarylphosphines, such as triphenylphosphine, trialkylphosphines, ethylenediamine, cyanide, carbon monoxide and carbon monosulfide.

Suitable metals include metals in the second or third row of the transition metals especially iridium, rhenium, rhodium and platinum.

The second or third row transition metals form organometallic complexes with carbon or nitrogen donors. These can include for example porphyrin and arylpyridines. For iridium metal cations the nitrogen donor is generally part of a heteroaromatic ring, such as pyridine or substituted pyridine, and the aryl is a phenyl, fused aryl, or more than one aromatic ring, or a heteroaryl, or a substituted equivalent. The dendron can be attached to either of the rings. The two rings of the "ligand" are normally in conjugation, so that the metal forms a 5 membered cyclometallated ring. Alternatively the rings can be attached in such a way that they can form a 6-membered cyclometallated ring with the metal cation. It is preferred that the at least two said dendrons are attached to ligands that are bonded to the metal by at least a carbon-metal bond. It is further preferred that the carbon-metal bond forms part of a cyclometallated ring. For the metal dendrimer the emission colour is governed by the lowest energy ligand. For green emission a suitable ligand and dendron attachment is shown in figure A of FIG. 6. For red emission it is appropriate to have 3 coordinating ligands each with a dendron attached to pyridine, for example as in Figure B. Alternatively for red emission there could be one ligand as in Figure B and two dendritic ligands as in Figure A and the Figure B type ligand may or may not have a dendron attached. For the blue emission it is suitable to have 3 coordinating ligands each with a dendron attached to the pyridine via say an ethylene link with, for example, fluoro groups on the phenyl, as shown in Figure C.

The dendrimers can be built in a convergent or divergent route, but a convergent route is preferred. Thus the dendrons are attached to the appropriate ligands and these are subsequently attached to the metal cation to form the dendritic metal complex. Optionally where the synthetic route allows other non-dendritic ligands can subsequently be attached to said complex. Alternatively a ligand with a suitably reactive functional group can be complexed to the metal ion, and then reacted with appropriately functionalised dendrons. In this latter method, not all ligands have to have the reactive functional groups, and thus this method allows the attachment of dendrons to some but not all of the ligands complexed to the metal. A key property of the dendrons is to impart solution processability to the metal complex and therefore allow the formation of good quality thin films suitable for use in light-emitting diodes.

The dendritic metal complexes may be homoleptic or contain more than one type of dendritic ligand, as discussed above. Alternatively, the metal complex may contain two or preferably more than two, e.g. 3, dendritic ligands plus one or more non-dendritic ligands. Also for iridium it is possible to have two dendritic phenylpyridine ligands with the third ligand a non-dendritic arylpyridine ligand. It is desirable that the number and/or generation of dendritic ligands is sufficient to provide the required solution processing. In the case of the dendritic metal complexes where all the ligands are different the method of preparation may give rise to a statistical mixture of all complex types. This is not necessarily disadvantageous providing that the optical, electronic, and processing properties are satisfactory. In the case of mixed dendron complexes it is preferable that the moieties forming the attachment point to metal are all the same or have similar binding constants. In the case of dendritic complexes that contain two or more different dendrons at least one should desirably be a conjugated dendron. The conjugated dendrons can be comprised of a number of different types of branching units, as discussed above.

The surface groups and dendrites can be varied so the dendrimers are soluble in solvents, such as toluene, THF, water and alcoholic solvents such as methanol, suitable for the solution processing technique of choice. Typically t-butyl and alkoxy groups have been used. In addition, the choice of dendron and/or surface group can allow the formation of blends with dendrimers (organic or organometallic), polymer or molecular compounds. In an alternative embodiment of the present invention the other blend component can be a charge transport material. If it is blended with another component the dendrimer of the current invention is preferably the major component in the blend by either weight % and/or mole %. If the dendrimer is blended with a polymer it is preferred that the polymer is a conjugated polymer or itself contains N as part of an aromatic ring or directly bonded to at least 2 aromatic rings.

According to another aspect of the present invention the organometallic dendrimer can be incorporated into a light emitting diode as either a homogeneous layer or as a blend with at least one dendrimer (organic or organometallic), polymer or molecular compound.

The organometallic dendrimers can be incorporated into an LED in a conventional manner. In its simplest form, an organic light emitting or electroluminescent device can be formed from a light emitting layer sandwiched between two electrodes, at least one of which must be transparent to the emitted light. Such a device can have a conventional arrangement comprising a transparent substrate layer, a transparent electrode layer, a light emitting layer and a back electrode. For this purpose the standard materials can be used. Thus, typically, the transparent substrate layer is typically made of glass although other transparent materials such as PET, can be used.

The anode which is generally transparent is preferably made from indium tin oxide (ITO) although other similar materials including indium oxide/tin oxide, tin oxide/antimony, zinc oxide/aluminum, gold and platinum can also be used. Conducting polymers such as PANI (polyaniline) or PEDOT can also be used.

The cathode is normally made of a low work function metal or alloy such as Al, Ca, Mg, Li, or MgAl or optionally with an additional layer of LiF. As is well known, other layers may also be present, including a hole transporting material and/or an electron transporting material. For a phosphorescent dendrimer emitter, it has been found that it is particularly beneficial to have a hole-blocking/electron-transporting layer between the light emitting dendrimer layer and the cathode. In an alternative configuration, the substrate may be an opaque material such as silicon and the light is emitted through the opposing electrode.

An advantage of the present invention is that the layer containing the dendrimer can be deposited from solution. Conventional solution processing techniques such as spin coating, ink-jet printing, printing, and dip-coating can be used to deposit the dendrimer layer. In a typical device a solution containing the dendrimer is applied over the transparent electrode layer, the solvent evaporated, and then subsequent layers applied. The film thickness is typically 10 nm to 1000 nm, preferably less than 200 nm, more preferably 30-120 nm.

The invention will be described in the Examples which follow, with reference to the accompanying drawings wherein:

EXAMPLE 1

DEHP-Car (1)

3,6-Di[4'-(2"-ethylhexyloxy)phenyl]carbazole

Figure 1:
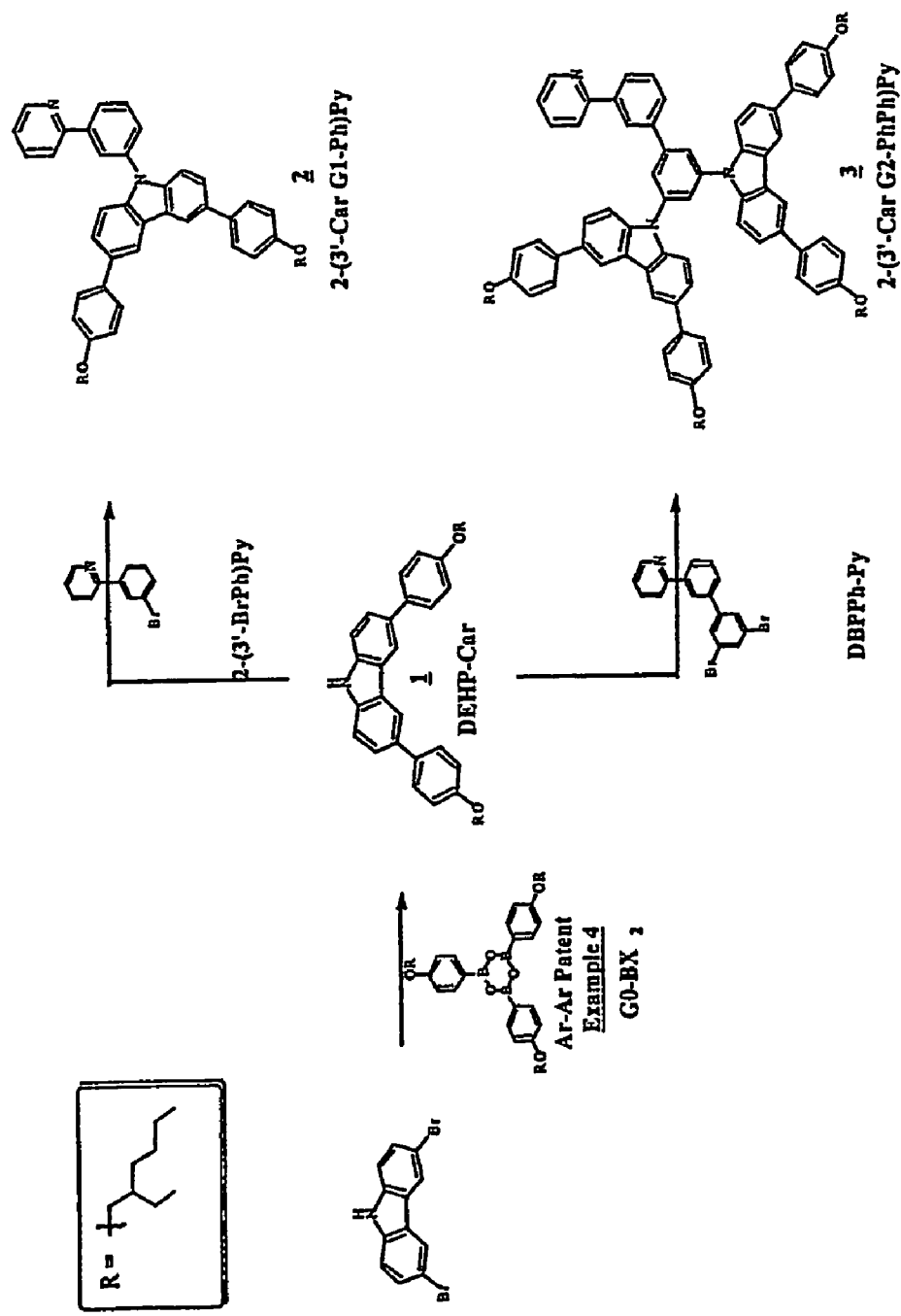
FIG. 1 illustrates the preparation of carbazolyl dendritic arylpyridine ligands (Examples 1 to 3) and a first generation iridium dendrimer. (Example 11)
Figure 1:
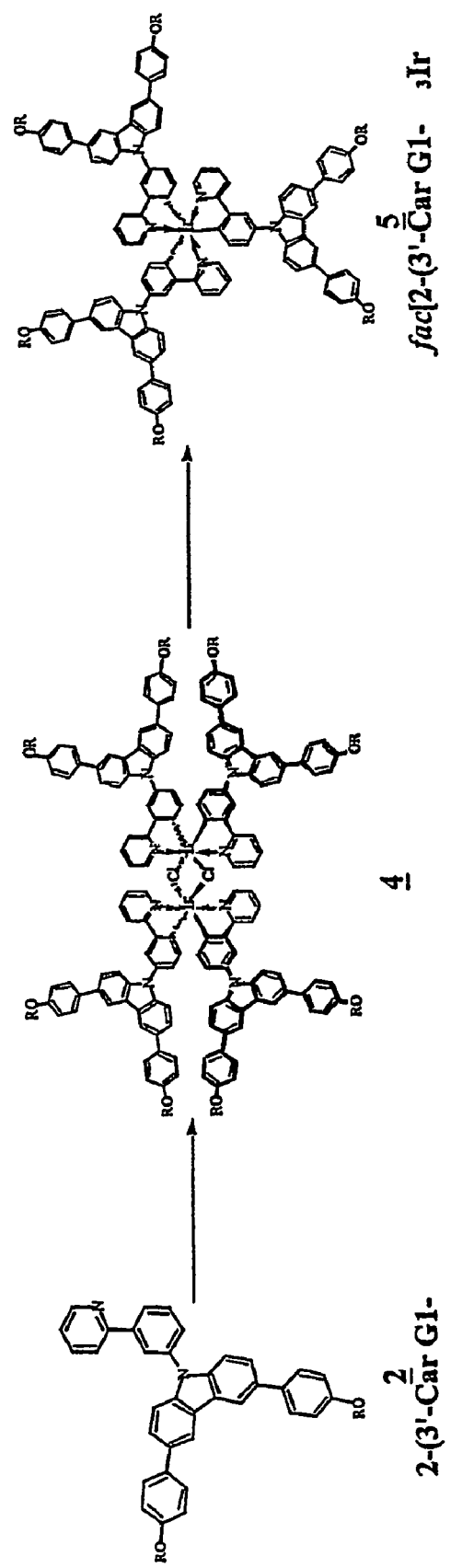
Figure 2:
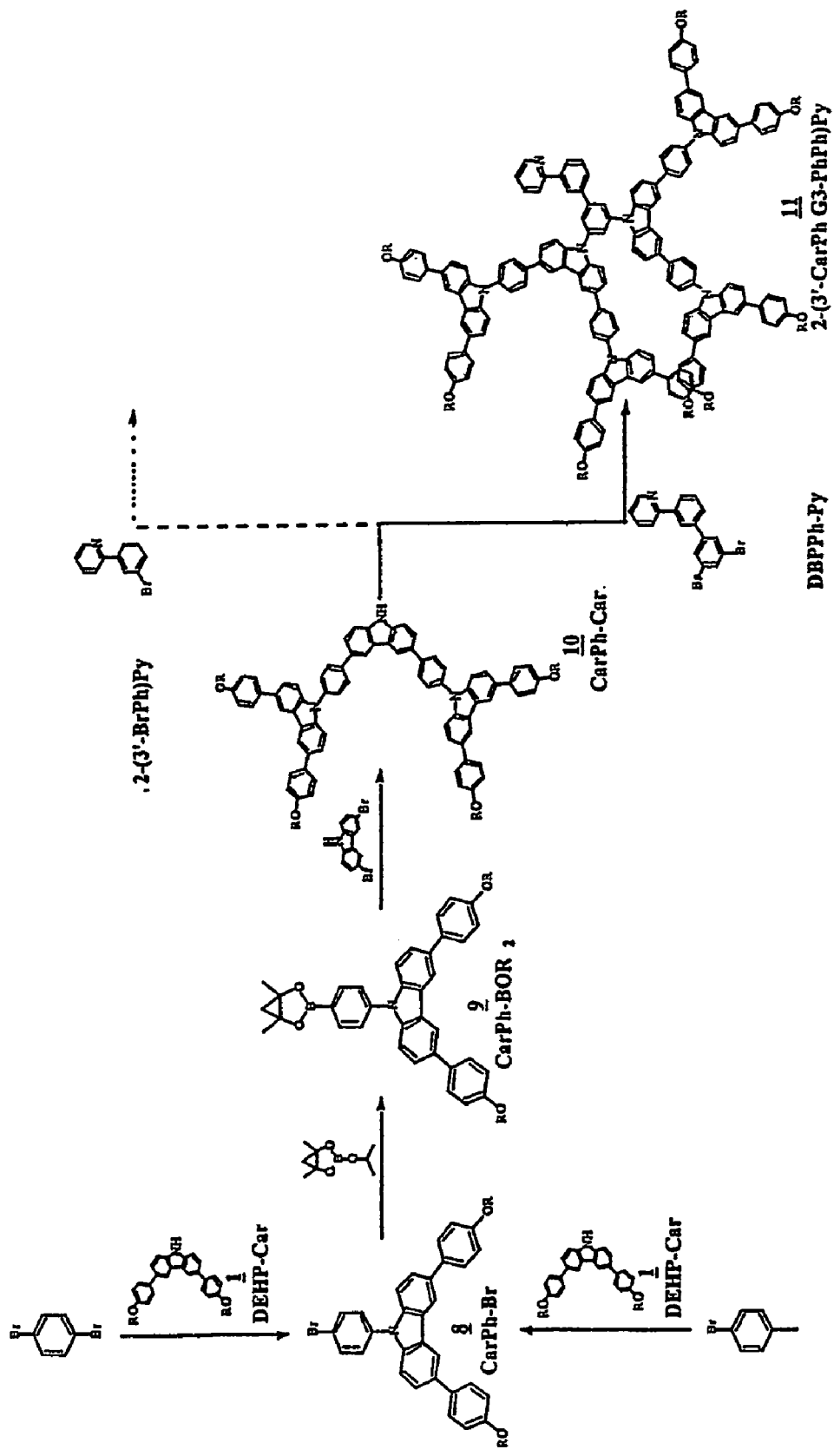
FIG. 2 illustrates the preparation of another carbazolyl arylpyridine dendritic ligand (Examples 4 to 8).
Figure 3:
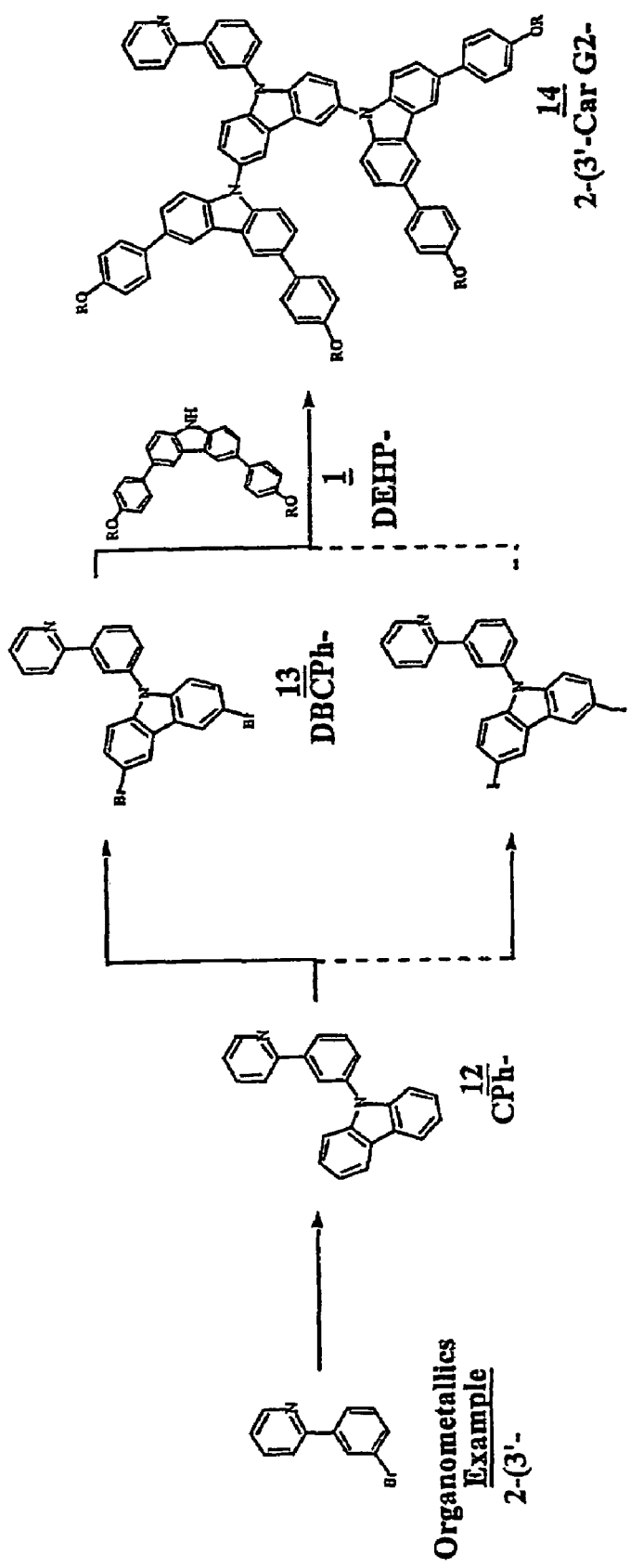
FIG. 3 illustrates the preparation of a second generation carbazolyl dendritic ligand and a first generation iridium dendrimer (Examples 9, 10).
Figure 4:
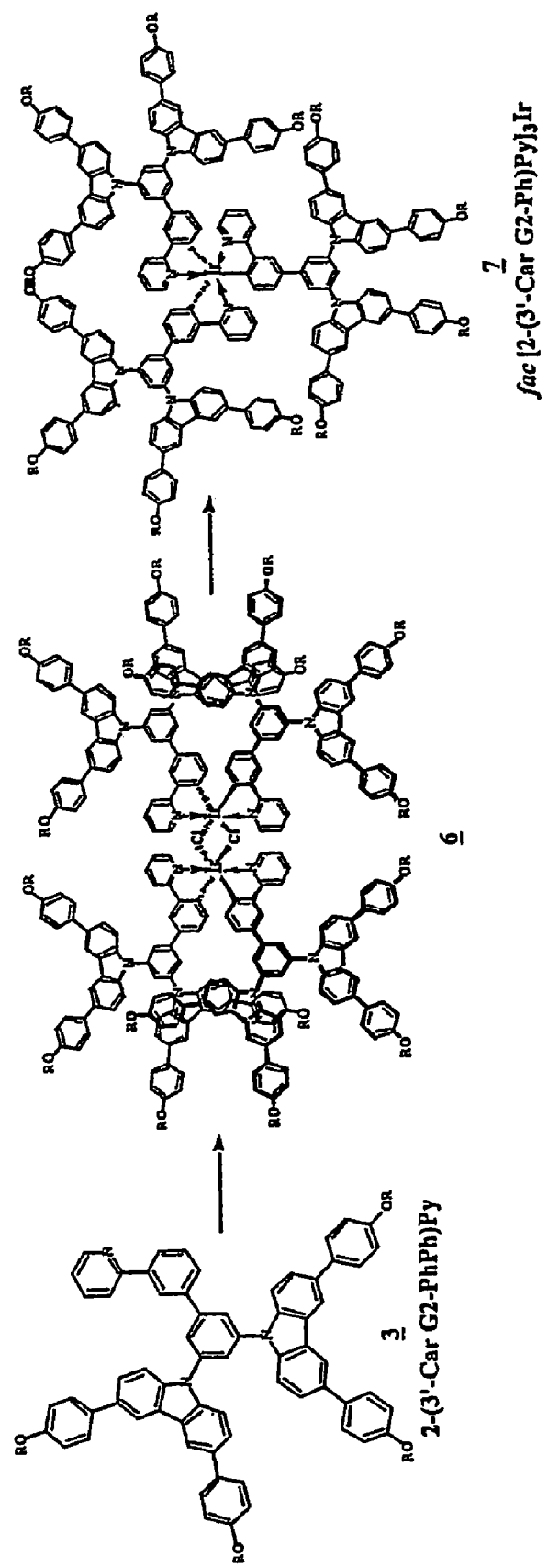
FIG. 4 illustrates the preparation of a second generation iridium dendrimer (Example 12).
Figure 5:
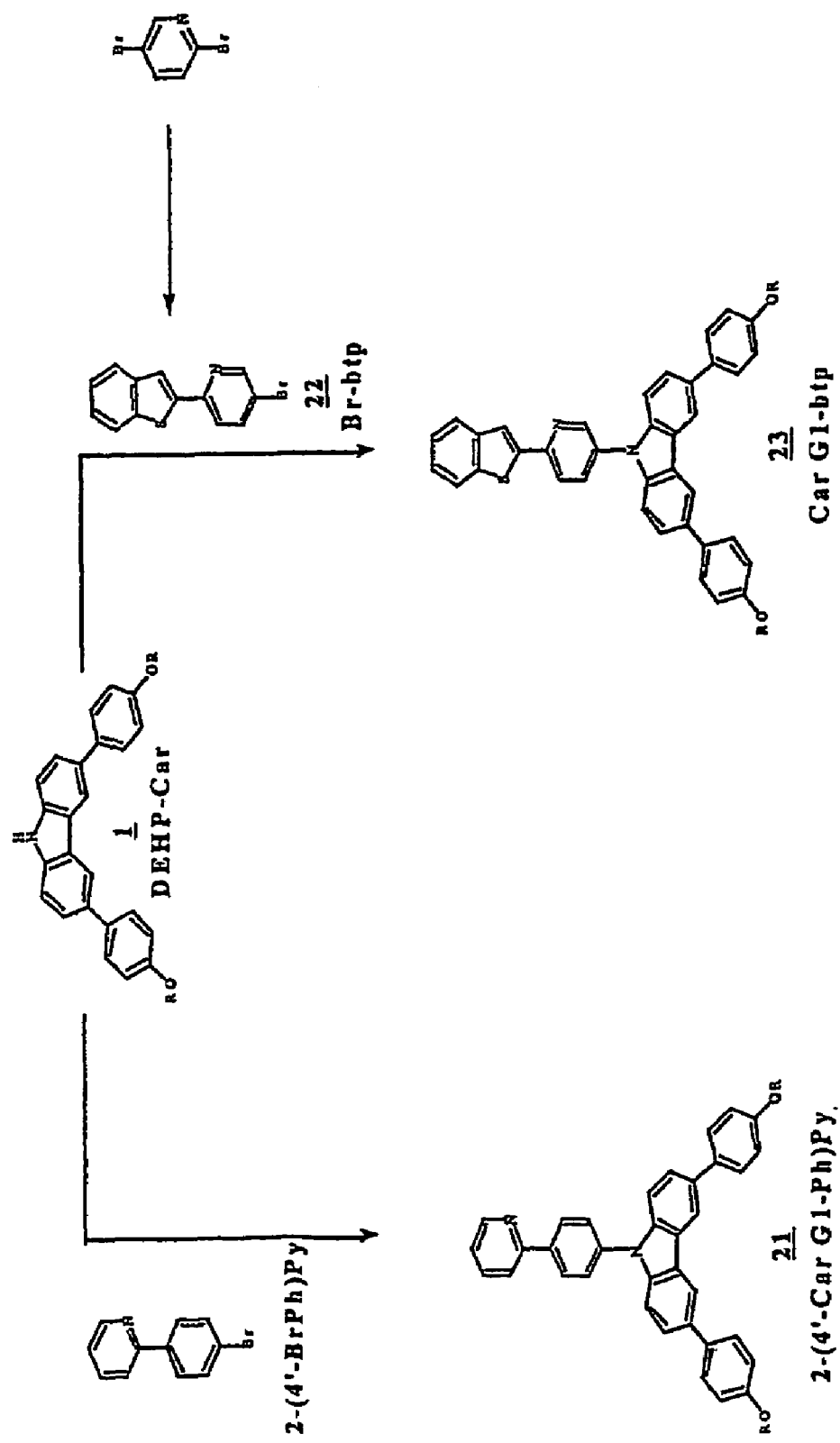
FIG. 5 illustrates the preparation of another first generation iridium dendrimer (Example 13-15).
Figure 5:
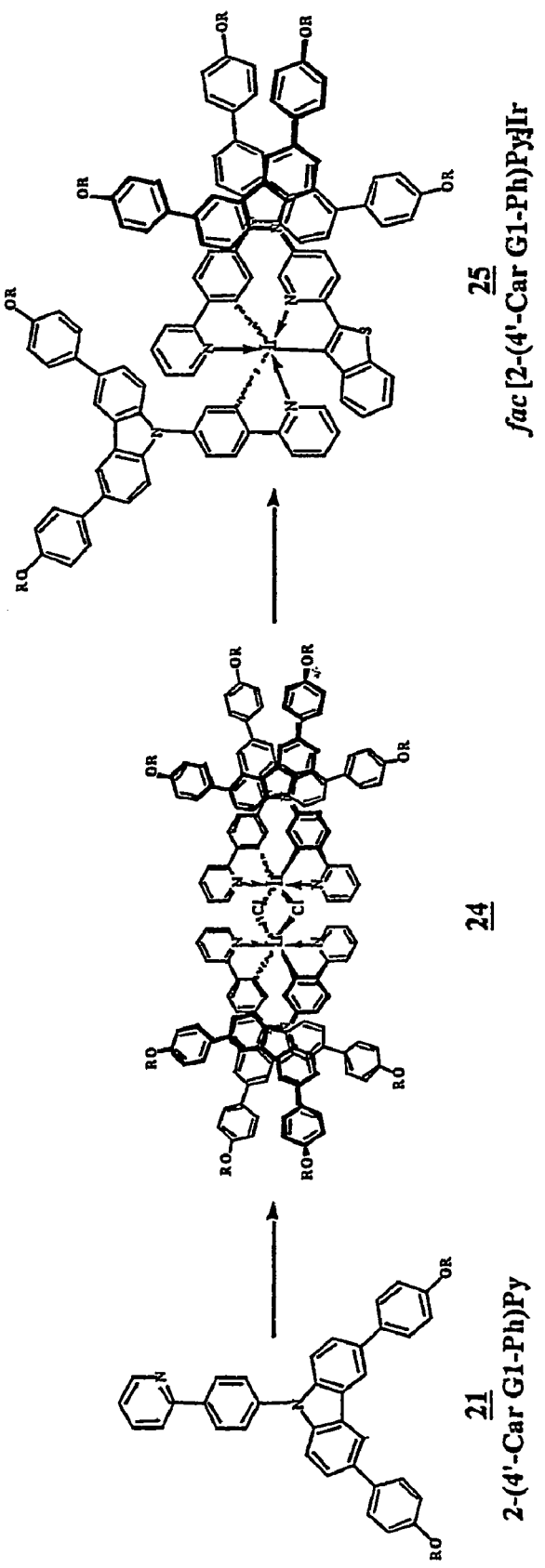
Figure 6:
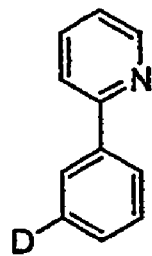
FIG. 6 illustrates suitable ligand and dendron attachments.
Figure 6:
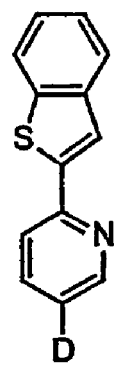
Figure 6:
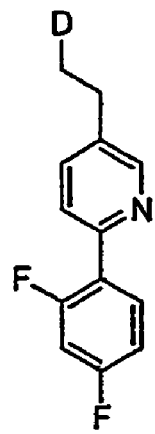
Figure 7:
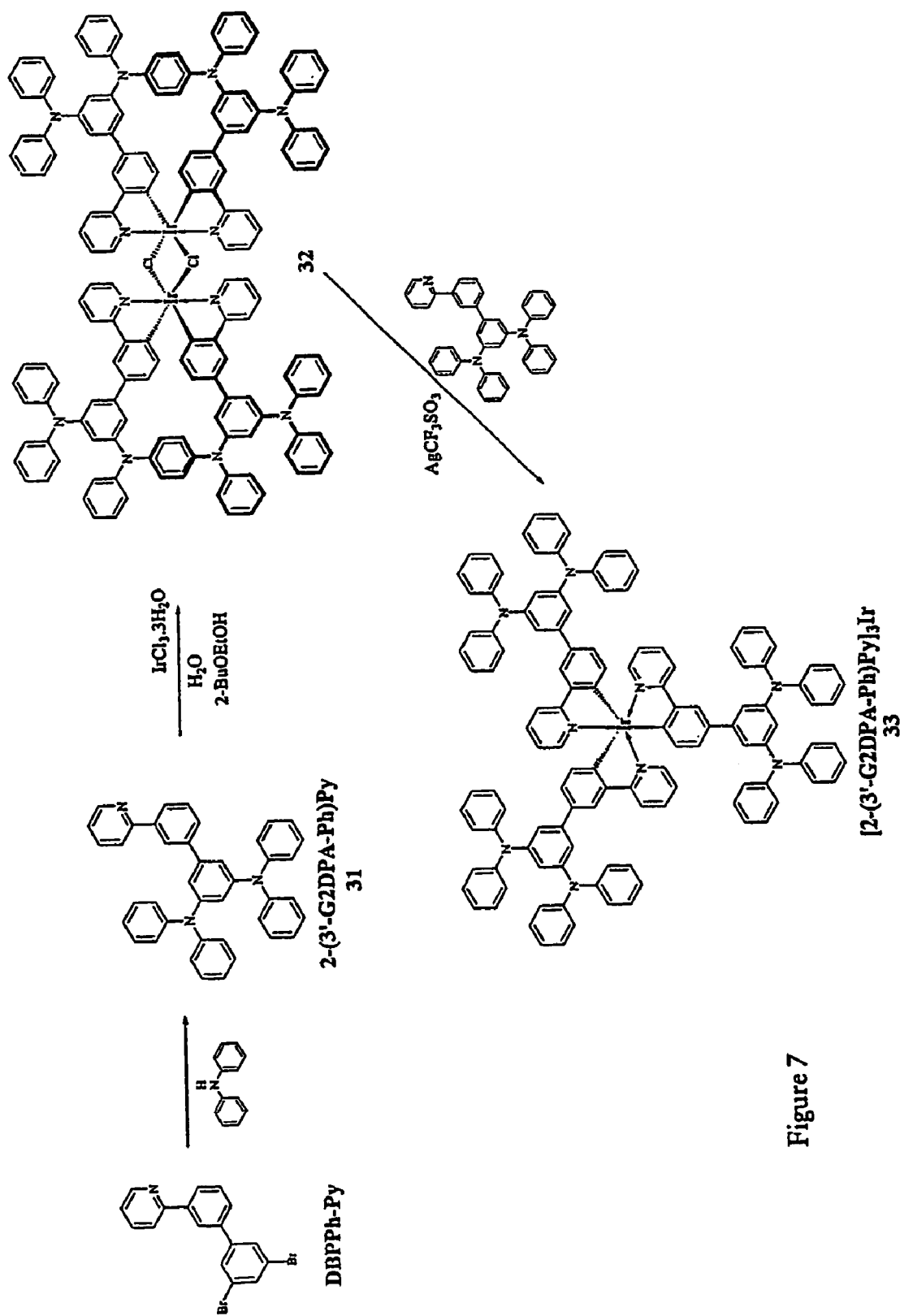
FIG. 7 illustrates the preparation of a second generation iridium dendrimer.

A mixture of 3,6-dibromocarbazole (12.0 g, 37.1 mmol), the boronic compound G0-BX$_2$, see below; (24.1 g, 96.4 mmol), tetrakis(triphenylphosphine) palladium (0) (800 mg, 0.692 mmol), 2 M Na$_2$CO$_{3(aq)}$ (40 cm$^3$), EtOH (40 cm$^3$) and toluene (100 cm$^3$) was degassed and then heated at reflux (with bath temperature of 100° C.) under argon for 42 h. The mixture was allowed to cool and diluted with H$_2$O (30 cm$^3$) and ether (40 cm$^3$). The two layers were separated. The aqueous layer was extracted with ether (3×40 cm$^3$). The organic layer and the ether extracts were combined, washed with brine (1×50 cm$^3$) and dried (Na$_2$SO$_4$) and filtered. The solvents were completely removed and the residue was purified by column chromatography over silica using ethyl acetate-light petroleum (0:1 to 1:10) and DCM-ethyl acetate-light petroleum (4:1:20) as eluent to give 14.7 g (69%) of 1; m/z [APCI$^+$] 576 (M$^+$).

G0-BX$_2$ was prepared as follows:

G0-Br 4-(2'-Ethylhexyloxy)phenylbromide

Sodium hydride (60% dispersion in oil, 17.4 g, 435 mmol) was added in portions to a cold (ice-bath) solution of 4-bromophenol (49.0 g, 283 mmol) in dry DMF (780 cm$^3$). The mixture was stirred at that temperature for 2 h and the ice bath was removed. A solution of 2-ethylhexylbromide (54.4 cm$^3$, 306 mmol) in 150 cm$^3$ of dry DMF was added dropwise through an addition funnel to the reaction mixture and the reaction was stirred at room temperature overnight (21 h). The resultant mixture was diluted with water (400 cm$^3$) and ether (500 cm$^3$). The two phases were separated. The aqueous layer was extracted with ether (3×300 cm$^3$) and the organic portion and the ether extracts were dried over anhydrous MgSO$_4$, filtered and the filtrate was collected and evaporated under reduced pressure to leave a yellow oil. Column chromatography over silica (half amount each time) with light petroleum as eluent afforded G0-Br (54.1 g, 67%) $\lambda_{max}$ (CH$_2$Cl$_2$)/nm 284 ($\epsilon$/dm$^3$mol$^{-1}$cm$^{-1}$ 1251), and 291sh (1001); $\delta_H$ (400 MHz; CDCl$_3$) 0.83-0.97 (6H, m, Me), 1.30-1.57 (8H, m, CH$_2$), 1.68-1.79 (1H, m, CH), 3.78-3.84 (2H, m, ArOCH$_2$), 6.74-6.80 (2H, m, ArH), and 7.33-7.40 (2H, m, ArH); $\delta_C$ (100 MHz; CDCl$_3$) 11.1, 14.1, 23.0, 23.8, 29.1, 30.4, 39.3, 70.7, 112.4, 116.3, 132.1, and 158.5.

G0-B(X)$_2$ 4-(2'-Ethylhexyloxy)phenylboronic acid

Tert-butyl lithium (1.7 M, 66.0 cm$^3$, 112 mmol) was added carefully to a cold (dry-ice/acetone bath) solution of G0-Br (20.0 g, 70.1 mmol) in 300 cm$^3$ of anhydrous THF under an argon atmosphere. The mixture was stirred at −78° C. for 1 h and then tri-methyl borate (57.2 cm$^3$, 421 mmol) was added slowly to the cold mixture. The reaction was stirred at −78° C. for 2 h before being removed from the dry-ice/acetone bath. The mixture was then stirred at room temperature for further 2.5 h before being quenched with 3 M $HCl_{(aq)}$ (30 cm$^3$). The two layers were separated. The aqueous layer was extracted with DCM (3×30 cm$^3$). The organic layer and the DCM extracts were combined and dried over anhydrous magnesium sulfate, filtered and the solvents were completely removed. Purification by column chromatography over silica using ethyl acetate-light petroleum (1:10), and then ethyl acetate-DCM (0:1 to 1:3) as eluent gave two major bands; less polar compound G0-B(X)$_2$A, 6.44 g; $\delta_H$ (200 MHz; CDCl$_3$) 0.81-1.05 (6H, m, Me), 1.22-1.62 (8H, m, CH$_2$), 1.68-1.88 (1H, m, CH), 3.91 (2H, m, ArOCH$_2$), 6.98 (2H, m, ArH), and 7.77 (2H, m, ArH); and more polar compound, a trimer, G0-B(X)$_2$B, 8.40 g; $\delta_H$ (200 MHz; CDCl$_3$) 0.85-1.07 (6H, m, Me), 1.30-1.64 (8H, m, CH$_2$), 1.70-1.90 (1H, m, CH), 3.95 (2H, m, ArOCH$_2$), 7.03 (2H, m, ArH), and 8.18 (2H, m, ArH).

Note: either compound G0-B(X)$_2$A or G0-B(X)$_2$B can be used in the reaction to form the next generation dendrons.

EXAMPLE 2

2-(3'-Car G1-Ph)Py (2)

2-(3'-{3",6"-Di[4'''-(2''''-ethylhexyloxy)phenyl]carbazolyl}phenyl)pyridine

Tris(dibenzylideneacetone)di-palladium (0) [Pd$_2$(dba)$_3$] (175 mg, 0.191 mmol) and tri-tert-butylphosphine (10% in hexane, 1.6 cm$^3$) were added to a degassed (Schlenk line, evacuated and back-filled with argon) mixture of carbazolyl compound 1 (3.50 g, 6.08 mmol), 2-(3'-bromophenyl)pyridine, 2-(3'-BrPh)Py, M. van der Sluis, V. Beverwijk, A Termaten, F. Bickelhaupt, H. kooijman, A. L. Spek, *Organometallics*, 1999, 18, 1402-1407; (2.85 g, 12.2 mmol), sodium tert-butoxide (1.75 g, 18.2 mmol), and freshly distilled toluene (from sodium under nitrogen) (6.0 cm$^3$). The dark purple mixture was degassed again before being heated at reflux (with bath temperature of 130-135° C.) under argon for 68 h. The mixture was allowed to cool and washed with H$_2$O (1×15 cm$^3$), dried (MgSO$_4$) and filtered and the solvent was removed. The mixture was purified by column chromatography over silica using DCM-light petroleum (1:4) as eluent to give 4.27 g (96%) of 2 as a light brown yellow oil; m/z [APCI$^+$] 729 M$^+$).

EXAMPLE 3

2-(3'-Car G2-PhPh)Py

2-[3'-(3",5"-Di{3''',6'''-di[4''''-(2'''''-ethylhexyloxy)phenyl]carbazolyl}phenyl)phenyl]pyridine Tris(dibenzylideneacetone)di-palladium (0) [Pd$_2$(dba)$_3$] (60 mg, 0.066 mmol) and tri-tert-butylphosphine (10% in hexane, 1.0 cm$^3$) were added to a degassed (Schlenk line, evacuated and back-filled with argon) mixture of carbazolyl compound 1 (3.55 g, 6.17 mmol), 2-[3'-(3",5"-dibromophenyl)phenyl]pyridine, DBPPh-Py see below; (1.00 g, 2.57 mmol), sodium tert-butoxide (988 mg, 10.3 mmol), and freshly distilled toluene (from sodium under nitrogen) (15 cm$^3$). The dark purple to brown mixture was degassed again before being heated (with bath temperature of 80° C. for 17 h) and then at reflux (with bath temperature of 130-135° C.) under argon for 5 days. The reaction was allowed to cool to room temperature and quenched with 5 cm$^3$ of H$_2$O. The mixture was purified by column chromatography over silica using DCM-light petroleum (0:1 to 1:40) as eluent to give 3.22 g (91%) of 3; (Found: C, 84.4; H, 7.8; N, 3.1. C$_{97}$H$_{107}$N$_3$O$_4$ requires C, 84.5; H, 7.8; N, 3.1%); $\delta_H$ (400 MHz; CDCl$_3$) 0.92-1.07 (24H, m, Me), 1.32-1.68 (32H, m, CH$_2$), 1.73-1.89 (4H, m, CH), 3.96 (8H, m, ArOCH$_2$), 7.08 (8H, m, ArH), 7.26-7.33 (1H, m, PyH), 7.61-8.14 (24H, m, ArH, CarH & PyH), 8.40 (1H, m, CarH), 8.46 (1H, m, ArH), and 8.74 (1H, m, PyH); $\delta_C$ (101 MHz; CDCl$_3$) 11.2, 14.2, 23.1, 23.9, 29.1, 30.6, 39.4, 70.6, 110.1, 114.9, 118.5, 120.7, 122.5, 123.5, 124.2, 124.4, 125.6, 126.0, 127.0, 127.7, 128.2, 129.7, 133.8, 134.1, 136.9, 139.8, 139.9, 140.1, 140.4, 144.7, 149.8, 156.8, and 158.6; m/z [MALDI] 1378, 1379, 1380, 1381, 1382 (M$^+$).

DBPPh-Py was prepared as follows:

PPh-BOR$_2$

2-[3'-(4",4",5",5"-tetramethyl-1",3",2"-dioxaborolan-2"-yl)phenyl]pyridine

Tert-butyl lithium (1.7 M, 36.6 cm$^3$, 62.1 mmol) was added to a cold (dry-ice/acetone bath) solution of 2-(3'-BrPh)Py (8.10 g, 34.6 mmol) in 130 cm$^3$ of anhydrous THF, under an argon atmosphere. The mixture was stirred at −78° C. for 2 h and then 2-isopropoxy-4,4,5,5-tetramethyl-1,3,2-dioxaborolane (9 cm$^3$) was added rapidly to the cold mixture. The reaction was stirred at −78° C. for 2 h and the dry-ice/acetone bath was removed. The mixture was then stirred at room temperature for further 20 h before being quenched with H$_2$O (30 cm$^3$). The two layers were separated. The aqueous layer was extracted with ether (3×40 cm$^3$). To the aqueous layer, NaCHO$_{3(sat)}$ (40 cm$^3$) was added and the aqueous layer was further extracted with ether (2×40 cm$^3$). The organic layer and the ether extracts were combined and dried over anhydrous sodium sulfate, filtered and the solvents removed. Purification of the crude mixture by column chromatography over silica using DCM-light petroleum (0:1 to 1:30) as eluent gave 4.92 g (50%) of PPh-BOR$_2$; (Found: C, 72.6; H, 7.2; N, 5.0. C$_{17}$H$_{20}$BNO$_2$ requires C, 72.6; H, 7.2; N, 5.0%); $\delta_H$ (400 MHz; CDCl$_3$) 1.37 (12H, s, Me), 7.23 (1H, m, PyH), 7.51 (1H, m, ArH), 7.76 (1H, m, PyH), 7.80 (1H, m, ArH), 7.87 (1H, m, PyH), 8.14 (1H, m, ArH), 8.40 (1H, m, ArH), and 8.71 (1H, m, PyH); $\delta_C$ (101 MHz; CDCl$_3$) 24.9, 83.9, 120.7, 122.0, 128.2, 129.9, 133.2, 135.3, 136.6, 138.7, 149.6, 154.6, and 157.5; m/z [APCI$^+$] 283 (MH$^+$).

DBPPh-Py

2-[3'-(3",5"-Di-bromophenyl)phenyl]pyridine

A mixture of PPh-BOR$_2$ (5.15 g, 281 mmol), 1,3,5-tribromobenzene (6.92 g, 315 mmol), tetrakis(triphenylphosphine) palladium (0) (846 mg, 0.732 mmol), 2 M Na$_2$CO$_{3(aq)}$ (12 cm$^3$), EtOH (12 cm$^3$) and toluene (48 cm$^3$) was degassed and then heated at reflux (with bath temperature of 105-110° C.) under argon for 19.5 h. The mixture was allowed to cool. Water (10 cm$^3$) and ether (20 cm$^3$) were added to the mixture. The two phases were separated. The aqueous layer was extracted with ether (3×20 cm$^3$). The organic layer and the ether extracts were combined and dried over anhydrous sodium sulfate and filtered. The solvents were completely removed. The residue was purified by column chromatography over silica using ethyl acetate-light petroleum (0:1 to 1:20) as eluent to give 4.70 g (66%) of DBPPh-Py; (Found: C, 52.6; H, 2.5; N, 3.6. C$_{17}$H$_{11}$Br$_2$N requires C, 52.5; H, 2.9; N, 3.6%); $\delta_H$ (400 MHz; CDCl$_3$) 7.29 (1H, m, PyH), 7.57 (2H, m, ArH), 7.67 (1H, m, ArH), 7.75 (2H, m, ArH), 7.79 (2H, m, PyH), 7.99 (1H, m, ArH), 8.19 (1H, m, ArH), and 8.74 (1H, m, PyH); $\delta_C$ (101 MHz; CDCl$_3$) 120.7, 122.5, 123.2, 125.7, 126.9, 127.6, 129.1, 129.4, 132.7, 136.9, 138.9, 140.2, 144.6, 149.8, and 156.8; m/z [EI] 386, 388, 390 (MH$^+$).

EXAMPLE 4

CarPh-Br (8)

4-{3',6'-Di[4"-(2'"-ethylhexyloxy)phenyl]carbazol}phenyl bromide

Method 1:

Tris(dibenzylideneacetone)di-palladium (0) [Pd$_2$(dba)$_3$] (125 mg, 0.137 mmol) and tri-tert-butylphosphine (10% in hexane, 0.5 cm$^3$) were added to a degassed (Schlenk line, evacuated and back-filled with argon) mixture of carbazolyl compound 1 [Example 1] (3.14 g, 5.45 mmol), 1,4-dibromobenzene (12.3 g, 52.2 mmol), sodium tert-butoxide (1.00 g, 10.4 mmol), and distilled xylenes (15 cm$^3$). The mixture was degassed again before being heated (with bath temperature of 135° C.) under argon for 115 h. The mixture was allowed to cool to ambient temperature and quenched with H$_2$O (0.5 cm$^3$). The mixture was purified by column chromatography over silica using light petroleum as eluent to give 1.46 g (37%) of 8; (Found: C, 76.1; H, 7.1; N, 2.1. C$_{46}$H$_{52}$BrNO$_2$ requires C, 75.6; H, 7.2; N, 1.9%); $\delta_H$ (400 MHz; CD$_2$Cl$_2$) 0.94-1.03 (12H, m, Me), 1.46-1.70 (16H, m, CH$_2$), 1.77-1.89 (2H, m, CH), 3.97 (4H, m, ArOCH$_2$), 7.07 (4H, m, ArH), 7.47 (2H, m, ArH), 7.52 (2H, m, CarH), 7.64-7.73 (6H, m, ArH), 7.79 (2H, m, CarH), and 8.41 (2H, m, CarH); $\delta_C$ (101 MHz; CD$_2$Cl$_2$) 11.8, 14.7, 23.9, 24.7, 29.9, 31.4, 40.3, 71.4, 110.7, 115.7, 119.0, 121.4, 124.9, 126.1, 128.8, 129.2, 133.9, 134.3, 134.6, 137.6, 140.9, and 159.5; m/z [MALDI$^+$] 730, 731, 732, 733, 734 MH$^+$).

Method 2:

Tris(dibenzylideneacetone)di-palladium (0) [Pd$_2$(dba)$_3$] (25 mg, 0.027 mmol) and tri-tert-butylphosphine (10% in hexane, 0.1 cm$^3$) were added to a degassed (Schlenk line, evacuated and back-filled with argon) mixture of carbazolyl compound 1 [Example 1] (628 mg, 1.09 mmol), 1-bromoiodobenzene (1.54 g, 5.45 mmol), sodium tert-butoxide (200 mg, 2.08 mmol), and distilled xylenes (3 cm$^3$). The mixture was degassed again before being heated (with bath temperature of 131° C.) under argon for 27 h. The resultant was allowed to cool to room temperature and quenched with H$_2$O (0.5 cm$^3$). The mixture was purified by column chromatography over silica using DCM-light petroleum (0:1 to 1:20) as eluent to give 476 mg (60%) of 8 as an oil; characterization data as above.

EXAMPLE 5

CarPh-BOR$_2$ (9)

2-(4-{3',6'-Di[4"-(2'"-ethylhexyloxy)phenyl]carbazolyl}phenyl)-(4,4,5,5-tetramethyl-1,3,2-dioxaborolane)

Tert-butyl lithium (1.7 M, 3.0 cm$^3$, 5.17 mmol) was added to a cold (dry-ice/acetone bath) solution of aryl bromide 8 (2.36 g, 3.23 mmol) in 22 cm$^3$ of anhydrous THF under an argon atmosphere. The mixture was stirred at −78° C. for 1 h and then 2-isopropoxy-4,4,5,5-tetramethyl-1,3,2-dioxaborolane (1.32 cm$^3$, 6.46 mmol) was added rapidly to the cold mixture. The reaction was stirred at −78° C. for 2 h before being removed from the dry-ice/acetone bath. The mixture was then stirred at room temperature overnight (12.5 h) before being quenched with H$_2$O (3 cm$^3$). One hour later, 10 cm$^3$ of ether and 20 cm$^3$ of brine were added to the mixture. The two layers were separated. The aqueous layer was extracted with ether (3×20 cm$^3$). The organic layer and the ether extracts were combined, washed with brine (1×40 cm$^3$) and dried over anhydrous sodium sulfate, filtered and the solvents were completely removed. Purification by column chromatography over silica using DCM-light petroleum (0:1 to 1:4) as eluent gave 1.24 g (49%) of 9; (Found: C, 80.3; H, 8.3; N, 1.8. C$_{52}$H$_{64}$BNO$_4$ requires C, 80.3; H, 8.3; N, 1.8%) $\delta_H$ (400 MHz; CDCl$_3$) 0.96-1.03 (12H, m, Me), 1.33-1.66 (28H, m, CH$_2$ & Me), 1.76-1.87 (2H, m, CH), 3.95 (4H, m, ArOCH$_2$), 7.07 (4H, m, ArH), 7.53 (2H, m, CarH), 7.62-7.71 (8H, m, ArH & CarH), 8.12 (2H, m, ArH), and 8.38 (2H, m, CarH), $\delta_C$ (101 MHz; CDCl$_3$) 11.2, 14.2, 23.1, 23.9, 24.9, 29.1, 30.6, 39.4, 84.1, 110.2, 114.9, 118.3, 124.2, 125.4, 125.8, 128.2, 133.5, 134.2, 136.4, 140.1, 140.4, and 158.5; m/z [MALDI] 777, 778, 779, 780, 781 (M$^+$).

EXAMPLE 6

CarPh-Car 3,6-di(4'-{3'",6"-di[4""-(2""'-ethylhexyloxy)phenyl]carbazolyl}phenyl)carbazole A mixture of 3,6-dibromocarbazole (196 mg, 0.604 mmol), 9 (1.08 g, 1.39 mmol), tetrakis(triphenylphosphine)palladium (0) (35 mg, 0.030 mmol), 2 M Na$_2$CO$_{3(aq)}$ (0.8 cm$^3$), EtOH (0.8 cm$^3$) and toluene (2.0 cm$^3$) was degassed and then heated at reflux (with bath temperature of 112° C.) under argon for 37 h. The resultant orange mixture was allowed to cool to room temperature and purified by column chromatography over silica using DCM-light petroleum (0:1 to 1:10) as eluent to give 571 mg (65%) of 10; $\delta_H$ (400 MHz; CDCl$_3$) 0.92-1.06 (24H, m, Me), 1.34-1.67 (32H, m, CH$_2$), 1.76-1.88 (4H, m, CH), 3.94 (8H, m, ArOCH$_2$), 7.06 (8H, m, ArH), 7.52-7.61 (6H, m, CarH & ArH), 7.64-7.76 (16H, m, ArH & CarH), 7.82 (2H, m, CarH), 7.98 (4H, m, CarH), 8.15 (1H, br s, NH), 8.39 (4H, m, CarH), and 8.52 (1H, m, CarH); $\delta_C$ (101 MHz; CDCl$_3$) 11.2, 14.2, 23.1, 23.9, 29.1, 30.6, 39.5, 70.6, 110.2, 111.3, 114.9, 118.3, 118.9, 124.1, 125.3, 125.6, 127.1, 128.2, 128.6, 132.2, 133.4, 134.3, 136.2, 139.6, 140.4, 141.0, and 158.6; m/z [MALDI] 1467, 1468, 1469, 1470, 1471 (MH$^+$).

EXAMPLE 7

2-(3'-CarPh G3-PhPh)Py (11)

2-(3'-{3"-5"-di[3'",6"'-di(4""-{3""',6""'-di[4"""''-(2"""''-ethylhexyloxy)phenyl]carbazolyl}phenyl)carbazolyl]phenyl}phenyl)pyridine Tris(dibenzylideneacetone)di-palladium (0) [Pd$_2$(dba)$_3$] (2.2 mg, 0.002 mmol) and tri-tert-butylphosphine (10% in hexane, 0.05 cm$^3$) were added to a degassed (Schlenk line, evacuated and back-filled with argon) mixture of carbazolyl compound 10 (339 mg, 0.231 mmol), 2-[3'-(3,5-dibromophenyl)phenyl]pyridine DBPPh-Py) (37.5 mg, 0.096 mmol), sodium tert-butoxide (37 mg, 0.385 mmol), and distilled xylenes (0.9 cm$^3$). The mixture was degassed again before being heated (with bath temperature of 121° C.) under argon for 3 days. The mixture was allowed to cool to room temperature and quenched with H$_2$O (0.2 cm$^3$). The mixture was purified by column chromatography over silica using DCM-light petroleum (0:1 to 1:20) as eluent to give 45 mg (15%) of 11; δ$_H$ (200 MHz; CDCl$_3$) 0.88-1.06 (48H, m, Me), 1.25-1.64 (64H, m, CH$_2$), 1.66-1.90 (8H, m, CH), 3.89 (16H, m, ArOCH$_2$), 7.03 (16H, m, ArH), 7.20-7.36 (1H, m, PyH), 7.48-8.13 (60H, m, CarH, ArH & PyH), 8.14-8.64 (17H, m, ArH & CarH), and 8.75 (1H, m, PyH); m/z [MALDI] 3160, 3161, 3162, 3163, 3164, 3165 (MH$^+$).

EXAMPLE 8

CPh-Py (12)

2-[3'-(N-Carbazolyl)phenyl]pyridine

Tris(dibenzylideneacetone)di-palladium (0) [Pd$_2$(dba)$_3$] (60 mg, 0.066 mmol) and tri-tert-butylphosphine (10% in hexane, 0.3 cm$^3$) were added to a degassed (Schlenk line, evacuated and back-filled with argon) mixture of carbazole (1.31 g, 7.82 mmol), 2-(3'-bromophenyl)pyridine (2-(3'-BrPh)Py) (610 mg, 2.61 mmol), sodium tert-butoxide (1.00 g, 10.4 mmol), and distilled toluene (15 cm$^3$). The mixture was degassed again before being heated (with bath temperature of 135° C.) under argon for 118 h. The mixture was allowed to cool to ambient temperature and quenched with H$_2$O (0.5 cm$^3$). The mixture was purified by column chromatography over silica using DCM-light petroleum (0:1 to 1:30) and then ethyl acetate-light petroleum (1:20) as eluent to give 835 mg (100%) of 12; δ$_H$ (200 MHz; CDCl$_3$) 7.21-7.92 (11H, m, PyH, CarH & ArH), 8.12-8.33 (4H, m, PyH, CarH & ArH), and 8.75 (1H, m, PyH); m/z [APCI$^+$] 321, 322, 323 (MH$^+$).

EXAMPLE 9

DBCPh-Py(13)

2-[3'-(3''-6''-Di-bromocarbazolyl)phenyl]pyridine

A solution of NBS (547 mg, 3.08 mmol) in 27 cm$^3$ of dried (over molecular sieves) DMF was added dropwise (over ~20 min) to a cold (ice-bath) solution of carbazolylphenylpyridine 12 (465 mg, 1.45 mmol) in 41 cm$^3$ of anhydrous DMF under argon. The mixture was stirred at 0-2° C. for 3.5 h and then ambient temperature for 42 h. The crude (brown mixture) was poured into 50 cm$^3$ of water and extracted with ether (3×100 cm$^3$). The ether extracts were combined, washed with brine (1×100 cm$^3$) and dried (Na$_2$SO$_4$), filtered and the solvents were removed to leave a brown solid. The crude residue was washed with light petroleum (3×100 cm$^3$). The solid was collected and dried under reduced pressure to give 540 mg (70%) of 13; δ$_H$ (200 MHz; CDCl$_3$) 7.23-7.40 (3H, m, PyH & CarH), 7.42-7.60 (3H, m, ArH & CarH), 7.62-7.78 (3H, m, PyH & ArH), 8.09-8.28 (4H, m, PyH, CarH & ArH), and 8.72 (1H, m, PyH); m/z [APCI$^+$] 477, 479, 481 (MH$^+$).

EXAMPLE 10

2-(3'-Car G2-Ph)Py (14)

2-[3'-(3''',''''-di{3''',6'''-Di[4''''-(2'''''-ethylhexyloxy)phenyl]carbazolyl}carbazolyl)phenyl]pyridine Tris(dibenzylideneacetone)di-palladium (0) [Pd$_2$(dba)$_3$] (12 mg, 0.013 mmol) and tri-tert-butylphosphine (10% in hexane, 0.2 cm$^3$) were added to a degassed (Schlenk line, evacuated and back-filled with argon) mixture of 2-[3'-(3''-6''-di-bromocarbazolyl)phenyl]pyridine 13 (280 mg, 0.586 mmol), DEHP-Car 1 (Example 1) (800 mg, 1.39 mmol), sodium tert-butoxide (200 mg, 2.08 mmol), and distilled xylenes (3 cm$^3$). The mixture was degassed again before being heated (with bath temperature of 133° C.) under argon for one week. The mixture was allowed to cool to room temperature and quenched with H$_2$O (0.5 cm$^3$). The crude was purified by column chromatography over silica using DCM-light petroleum (0:1 to 1:10) as eluent to give ≈173 mg (≈20%) of 14; δ$_H$ (200 MHz; CDCl$_3$) 0.82-1.05 (24H, m, Me), 1.24-1.64 (32H, m, CH$_2$), 1.66-1.89 (4H, m, CH), 3.92 (8H, m, ArOCH$_2$), 7.03 (8H, m, ArH), 7.28-7.93 (26H, m, PyH, CarH & ArH), 8.18-8.47 (7H, m, ArH, PyH & CarH), and 8.78 (1H, m, PyH); m/z [MALDI] 1468, 1469, 1470, 1471, 1472 (MH$^+$).

EXAMPLE 11

Fac [2-(3'-Car G1-Ph)Py]$_3$Ir (5)

Fac tris[2-(3'-{3'',6''-di[4'''-(2''''-ethylhexyloxy)phenyl]carbazolyl}phenyl)pyridine] iridium (III)

A mixture of the 2-(3'-Car G1-Ph)Py 2 [Example 2] (3.25 g, 4.46 mmol), iridium chloride tri-hydrate (314 mg, 0.892 mmol), H$_2$O (7.0 cm$^3$) and 2-ethoxyethanol (23 cm$^3$) was heated (bath temperature: 127° C.) under argon for 40 h. The resultant orange mixture was allowed to cool to ambient temperature to precipitate the orange solid. The filtrate was separated and the 2-ethoxyethanol removed under high vacuum. The residue was purified by column chromatography over silica with DCM-light petroleum (1:30 to 0:1) as eluent to give 244 mg of the excess ligand 2 and 110 mg of the desired dichloro-bridged dimer 4. The orange solid was purified by column chromatography over silica with DCM-light petroleum (0:1 to 1:0) as eluent to give 1.02 g of 4. This was combined with the other fraction of 4 to give 1.13 g (75%); δ$_H$ 0.86-1.01 (48H, m, Me), 1.28-1.63 (64H, m, CH$_2$), 1.71-1.87 (8H, m, CH), 3.92 (16H, m, ArOCH$_2$), 6.37 (4H, m, ArH), 6-99-7.09 (24H, m, ArH & PyH), 7.37 (8H, m, CarH), 7.54 (8H, m, CarH), 7.63 (16H, m, ArH), 7.78-7.87 (8H, m, PyH & CarH), 7.91 (4H, m, PyH), 8.35 (8H, m, CarH), and 9.48 (4H, m, PyH); δ$_C$ (101 MHz; CDCl$_3$) 11.2, 14.1, 23.1, 23.9, 29.1, 30.6, 39.4, 70.6, 110.0, 114.8, 118.2, 119.1, 122.4, 123.2, 123.7, 125.2, 128.2, 131.9, 132.1, 133.0, 134.3, 137.1, 140.7, 144.3, 145.4, 151.9, 158.4, and 167.8; m/z A mixture of the above obtained iridium complex 4 (910 mg, 0.540 mmol) and 2-3'-Car G1-Ph)Py 2 (1.66 g. 2.28 mmol) and silver trifluoromethanesulfonate (277 mg, 1.08 mmol) was heated (bath temperature: 145° C.) for 6.5 days under argon. The reaction was then allowed to cool to room temperature. The dark brown mixture was purified by column chromatography over silica with DCM-light petroleum (0:1 to 1:4) as eluent to give 631 mg (49%) 5; TGA$_{(5\%)}$ 420° C.; λ$_{max}$/nm (thin film) 265 and 297; δ$_H$ (400 MHz; CD$_2$Cl$_2$) 0.92-1.04 (36H, m, Me), 1.33-1.67 (48H, m, CH$_2$), 1.78-1.87 (6H, m, CH), 3.94 (12H, m, ArOCH$_2$), 7.03 (4H, m, ArH), 7.11 (1H, m, PyH), 7.26 (1H, m, ArH) 7.42 (1H, m, ArH), 7.46-7.75 (9H, m, CarH, ArH & PyH), 7.80 (1H, m, PyH), 7.92 (1H, m, PyH), 7.97 (1H, m, ArH) and 8.41 (1H, m, PyH);

EXAMPLE 12

Fac [2-(3'-Car G2-Ph)Py]₃Ir (7)

Fac tris{2-[3'-(3",5"-di{3''',6'''-di[4''''-(2'''''-ethylhexyloxy)phenyl]carbazolyl}phenyl)phenyl]pyridine} iridium (III)

A mixture of 2-(3'-Car G2-Ph)Py 3 (734 mg, 0.532 mmol), iridium chloride tri-hydrate (38 mg, 0.106 mmol), H₂O (1.5 cm³) and 2-butoxyethanol (6.5 cm³) was heated (bath temperature: 140° C.) under argon for 3 days before being cooled. The yellow precipitate was filtered off and washed with 95% of EtOH (~10 cm³). The yellow solid was dissolved into 5 cm³ of DCM and purified by column chromatography over silica using DCM-light petroleum (0:1 to 1:4) as eluent to give 85.2 mg (27%) of a brown yellow solid as the dichloro-bridged dimer 6; m/z [MALDI] 2949 (broad) ($C_{194}H_{212}IrN_6O_8$—Cl⁺). Moreover, a light yellow-brown solid was isolated (589 mg, 80%) as the excess ligand 3. A mixture of the above obtained iridium complex (80 mg, 0.27 mmol) and the recycled 2-(3'-Car G2-Ph)Py 3 (589 mg, 0.427 mmol) and silver trifluoromethanesulfonate (15 mg, 0.058 mmol) was heated (bath temperature: 160° C.) for 5.5 days under argon. The reaction was then allowed to cool to room temperature. The mixture was dissolved into 10 cm³ of DCM and purified by column chromatography over silica with DCM-light petroleum (0:1 to 1:0) as eluent to give 78 mg (67%) of solid as 7; $\lambda_{max}$/nm (thin film) 261 and 298; $\delta_H$ (500 MHz; CDCl₃) 0.89-1.00 (72H, m, Me), 1.30-1.60 (96H, m, CH₂), 1.72-1.84 (12H, m, CH), 3.90 (24H, m, ArOCH₂), 6.92-7.03 (30H, m, ArH & PyH), 7.17 (3H, m, PArH) 7.37 (3H, m, PyH), 7.59-7.69 (51H, m, ArH & CarH), 7.77 (3H, m, ArH), 8.10-8.07 (12H, m, ArH), and 8.34 (4H, m, CarH); m/z [MALDI] 4327 (broad) (MH⁺). Excess ligand 3 was isolated as a light yellow-brown solid (380 mg)

EXAMPLE 13

2-(4'-Car G1-Ph)Py (21)

2-(4'-{3",6"-Di[4'''-(2''''-ethylhexyloxy)phenyl]carbazolyl}phenyl)pyridine

Tris(dibenzylideneacetone)di-palladium (0) [Pd₂(dba)₃] (114 mg, 0.124 mmol) and tri-tert-butylphosphine (10% in hexane, 0.7 cm³) were added to a degassed (Schlenk line, evacuated and back-filled with argon) mixture of DEHP-Car 1 [Example 1] (3.27 g, 5.68 mmol), 2-(4'-bromophenyl)pyridine 2(4'-BrPh)Py (2.66 g, 11.4 mmol) M. A. Gutierrez, G. R. Newkome, J. Selbin, *J. Organomet. Chem.*, 1980, 202, 341-350, sodium tert-butoxide (1.64 g, 17.1 mmol), and distilled toluene (from sodium under nitrogen) (6.0 cm³). The dark purple mixture was degassed again before being heated at reflux (with bath temperature of 90° C. for 48 h and then 140° C. for anther 3 days under argon. The mixture was allowed to cool and washed with H₂O (1×15 cm³), dried (MgSO₄), filtered and the solvent removed. The mixture was purified by column chromatography over silica using DCM-light petroleum (1:0 to 1:10) as eluent to give 2.87 g (69%) of 21 as light brown yellow oil; m/z [APCI⁺] 729 (M⁺).

EXAMPLE 14

Br-btp (22)

A mixture of 2,5-di-bromopyridine (4.43 g, 18.7 mmol), thianaphthene-2-boronic acid (4.00 g, 22.5 mmol), tetrakis (triphenylphosphine) palladium (0) (886 mg, 0.749 mmol), 2 M Na₂CO₃$_{(aq)}$ (18 cm³), EtOH (18 cm³) and toluene (50 cm³) was degassed and heated at reflux (with bath temperature of 102° C.) under argon for 20 h. The mixture was allowed to cool. The reaction precipitate mixture was filtered off and the precipitate washed with light petroleum. The solid was dried under vacuum to give 4.53 g (83%) of 22.

Car G1-btp (23)

Tris(dibenzylideneacetone)di-palladium (0) [Pd₂(dba)₃] (50 mg, 0.055 mmol) and tri-tert-butylphosphine (10% in hexane, 0.8 cm³) were added to a degassed (Schlenk line, evacuated and back-filled with argon) mixture of DEHP-Car (1) (1.90 g, 3.30 mmol), Br-btp (22) (300 mg, 1.03 mmol), sodium tert-butoxide (348 mg, 3.62 mmol), and distilled toluene (from sodium under nitrogen) (2.0 cm³). The mixture was degassed again before being heated at reflux (with bath temperature of 112° C.) for 7.5 days under argon. The mixture was allowed to cool and 30 cm³ of DCM was added. H₂O (0.5 cm³) was added to the mixture. The mixture was then concentrated to about 10 cm³ and purified by column chromatography over silica using DCM-light petroleum (1:40 to 1:20) as eluent to give 156 mg (19%) of 23; $\delta_H$ (200 MHz; CDCl₃) 0.83-1.08 (12H, m, Me), 1.27-1.63 (16H, m, CH₂), 1.70-1.89 (2H, m, CH), 3.93 (4H, m, ArOCH₂), 7.05 (4H, m, ArH), 7.38-7.52 (4H, m, ArH & CarH), 7.54-7.72 (6H, m, ArH), 7.81-8.03 (5H, m, CarH, ArH & PyH), 8.37 (2H, m, CarH), and 8.94 (1H, m, PyH; m/z (APCI⁺] 729 (M⁺).

EXAMPLE 15

Fac [2-(4'-Car G1-Ph)Py]₃Ir (25)

Fac tris[2-(4'-{3",5"-di[4'''-(2''''-ethylhexyloxy(phenyl]carbazolyl}phenyl)pyridine] iridium (III)

A mixture of 2-(4'-Car G1-Ph)Py 21 (2.57 g, 3.53 mmol), iridium chloride tri-hydrate (560 mg, 1.59 mmol), H₂O (5 cm³) and 2-butoxyethanol (30 cm³) was heated (bath temperature: 125-141° C.) under argon for 48 h. The resultant orange mixture was allowed to cool to ambient temperature to precipitate the orange solid. The solid was filtered and washed with 95% of EtOH. Further purification of the residue by column chromatography over silica with DCM-light petroleum (0:1 to 1:0) as eluent gave the dichloro-bridged dimer 24; $\delta_H$ (400 MHz, CDCl₃) 0.93-1.01 (48H, m, Me), 1.32-1.64 (64H, m, CH₂), 1.73-1.88 (8H, m, CH), 3.93 (16H, m, ArOCH₂), 6.28 (4H, m, ArH), 7.75 (4H, m, PyH), 7.01 (16H, m, ArH), 7.12 (4H, m, ArH), 7.33 (8H, m, CarH), 7.51 (8H, m, CarH), 7.58-7.70 (20H, m, ArH), 7.74 (4H, m, PyH), 7.90 (4H, m, PyH), 8.25 (8H, m, CarH), and 9.49 (4H, m, PyH); $\delta_C$ (101 MHz; CDCl₃) 11.2, 14.1, 23.1, 23.9, 29.1, 30.6, 39.4, 70.6, 110.7, 114.8, 117.9, 119.1, 119.2, 124.0, 125.0, 127.7, 128.1, 133.1, 134.3, 137.0, 137.8, 139.6, 142.6, 146.3, 151.3, 158.5, and 167.5;

Using a method similar to that described in Example 11, the dichloro-bridged dimer 24 can then be used to form the dendrimer 25.

EXAMPLE 16

| Compound | Device structure | Peak efficiency (PE) (cd/A) (±10%) | Voltage at PE | Brightness at PE (cd/m²) | Max brightness and voltage cd/m² at V | Turn on voltage (V) |
|---|---|---|---|---|---|---|
| 5 G1-IrppyCarb | ITO/5 (45 nm)/Ca (20 nm)/Al (100 nm) | 9.8 | 6.8 | 472 | 6130 at 11.8 | 3.6 |
| 5 G1-IrppyCarb | ITO/5 (45 nm)/TPBI (45 nm)/LiF (0.6 nm)/Ca (20 nm)/Al (100 nm) | 12.9 | 4.8 | 156 | 11730 at 13.8 | 3 |
| 7 G2-IrppyCarb | ITO/7 (45 nm)/Ca (20 nm)/Al (100 nm) | 22 | 13 | 10910 | 11990 at 13.4 | 5.4 |
| 7 G2-IrppyCarb | ITO/7 (45 nm)/TPBI (45 nm)/LiF (0.6 nm)/Ca (20 nm)/Al (100 nm) | 13 | 10 | 99 | 3700 at 20 | 6.4 |
| Comparative Ir-G2 | ITO/G2-Ir (120 nm_/Ca (20 nm)/Al (100 nm | 7 | 12 | 1250 | >6000 @ 17 | 4.2 |

The device was prepared as follows:

1. Etch ITO squares 12×12 mm into 4×12 mm ITO strip by acid etch

2. Acetone rinse for 10 minutes with ultrasonication

3. Propan-2-ol rinse for 10 minutes with ultrasonication

4. Substrates dried under dry nitrogen flow

5. Substrates subject to oxygen plasma treatment for 5 minutes at 100 W

6. Dendrimer film deposited by spin coating

7. Substrates placed in vacuum evaporator 8. 20 nm of calcium deposited at 0.1 nm/s under vacuum of $1 \times 10^{-6}$ mBar 9. 100 nm of aluminium deposited at 0.1 nm/s under vacuum of $1 \times 10^{-6}$ mBar The table shows the performance of devices made with two types of dendrimer according to the current invention (compounds 5 and 7) and a comparative example for a device made with an Ir-cored dendrimer (Ir-G1) that does not have N atoms as part of units in the dendrons.

Ir-G2 is fac tris{2-[3'-(3",5"-di{3''',5'''-di[4''''-2''''-ethylhexyloxy)phenyl]phenyl}phenyl) Phenyl]pyridine}iridium (III) which is a second generation dendrimer. Ir-G1 is fac tris [2-3'-{3",5"-di[4'''-(2''''-ethylhexyloxy)phenyl] phenyl}phenyl)pyridine]iridium (III) which is a first generation dendrimer. (The synthesis of these dendrimers is given in the PCT application claiming priority from GB 0104175.5).

As can be seen from the table the efficiency of a device containing a neat layer of the second generation dendrimer 7 is greater than that of a device containing a neat layer of the first generation dendrimer 5. Both of the devices based on the new dendrimers show better efficiency than the comparative example. Although not shown a device with a neat layer of Ir-G1 has a lower efficiency than a device with a neat layer of Ir-G2. These results clearly show that Ir dendrimers that have dendrons containing carbazole units offer marked benefits over the previously known Ir dendrimers.

Photoluminescent quantum yield (PLQY) of Green Ir-Dendrimers in Neat Films

| Dendrimer | PLQY % |
|---|---|
| Ir-G1 | 22 |
| Ir-G2 | 31 |
| Ir-Carb G1 5 | 48 |
| Ir-Carb G2 7 | 35 |

These film PLQYs were measured in an integrating sphere following excitation at 325 nm. The PLQYs are higher for both the carbazole-type dendrimer films than the non-carbazole-type iridium dendrimer films, with the most marked increase (22% to 48%) shown by the first generation dendrimers.

Compound 5 undergoes a number of chemically reversible electrochemically quasi-reversible oxidations in dry inert conditions, whereas under the same conditions both fac tris (2-phenylpyridine) iridium (III) and the dendrimer Ir-G1 each only undergo one chemically reversible electrochemically quasi-reversible oxidation. However the reduction behaviour of 5 is very similar to the behaviour of the non-carbazole-type first generation iridium dendrimer IR-G1.

EXAMPLE 17

G1-Ir-Carbazole (5) of Example 11 and G2-Ir-Carbazole (7) of Example 12 were used in single-layer OLED devices. They were obtained from a 15 mg/ml solution in chloroform and spin coated at 2000 rpm for 60 seconds to provide the structure ITO/Dendrimer/Ca/Al. The thickness of the layer of compound 5 was about 45 nm and that of compound 7 about 65 nm. The CIE coordinates obtained are x=0.340, y=0.610 for G1-Ir-carbazole (5) and x=0.332, y=0.628 for G2-Ir-Carbazole (7).

EXAMPLE 18

2-(3'-G2DPA-Ph)Py (31)

2-{3'-[3",5"-Di(diphenylamino)phenyl] phenyl}pyridine

Tris(dibenzylideneacetone)di-palladium (0) [Pd$_2$(dba)$_3$] (135 mg, 0.148 mmol) and tri-tert-butylphosphine (10% in hexane, 3 cm$^3$) were added to a deoxygenated (Schlenk line, evacuated and back-filled with argon) mixture of diphenylamine (1.40 g, 8.27 mmol), 2-[3'-(3",5"-dibromophenyl)

phenyl]pyridine DBPPh-Py (1.15 g, 2.96 mmol), sodium tert-butoxide (1.14 g, 14.8 mmol), and anhydrous toluene (32 cm$^3$). The mixture was deoxygenated again before being heated at reflux (with bath temperature of 128° C.) under argon for 20 h. The mixture was allowed to cool and quenched with H$_2$O (1 cm$^3$). The mixture was concentrated to about 2 cm$^3$ and purified by column chromatography over silica gel using NEt$_3$-DCM-light petroleum (0:0:1 to 0.001:1:4) as eluent to give 1.61 g (96%) of 31 as a light brown solid; $1_{max}$/nm (thin film) 301; d$_H$ (200 MHz; CDCl$_3$) 6.85 (1H, m, ArH), 6.92-8.05 (29H, m, PyH & ArH), and 8.69 (1H, m, PyH); m/z [APCI$^+$] 565 (M$^+$).

EXAMPLE 19

[2-(3'-G2DPA-Ph)Py]$_3$Ir (33)

Fac tris(2-{3'-[3",5"-di(diphenylamino)phenyl]phenyl}pyridine) iridium (III)

A mixture of the ligand 2-(3'-G2DPA-Ph)Py 31 (300 mg, 0.530 mmol), iridium chloride tri-hydrate (75 mg, 0.212 mmol), H$_2$O (4 cm$^3$) and 2-butoxyethanol (12 cm$^3$) was heated (bath temperature: 125° C.) under argon for 17 h before being cooled. Ethanol (90%, 10 cm$^3$), was added to the mixture. The precipitate was filtered off and washed with ethanol (~50 cm$^3$). The solid was purified by a silica gel column using DCM-light petroleum (1:10 to 1:4) as eluent to give the chloro-bridged dimer 32 (141 mg) as a yellow solid; d$_H$ (200 MHz; CDCl$_3$) 5.83 (4H, m, ArH), 6.50-7.85 (112H, m, PyH & ArH), and 9.15 (4H, m, PyH); m/z [MALDI] 1320, 1321, 1322, 1323, 1324, 1325, (C$_{82}$H$_{60}$IrN$_6^+$), 1356, 1357, 1358, 1359, 1360 (C$_{82}$H$_{60}$ClIrN$_6$).

A mixture of the chloro-bridged dimer 32 (141 mg), 2-{3'-[3",5"-di(diphenylamino)phenyl]phenyl}pyridine (235 mg, 0.417 mmol), and silver trifluoromethanesulfonate (53 mg, 0.208 mmol) was heated (bath temperature: 156-160° C.) for 6.5 days under argon. The reaction was allowed to cool to room temperature. The mixture was dissolved in ~3 cm$^3$ of DCM and purified on silica gel column using DCM-light petroleum (1:10 to 1:5) as eluent to give 86 mg (44%) of 33 as a yellow solid; $1_{max}$/nm (thin film) 303; d$_H$ (200 MHz; CD$_2$Cl$_2$) 6.60-6.78 (9H, ArH & PyH), 6.83-7.28 (69H, m, ArH, & PyH), 7.45-7.66 (9H, m, ArH, & PyH), and 7.83 (3H, m, PyH); m/z [MALDI] 1885, 1886, 1887, 1888, 1889, 1890 (M$^+$).

EXAMPLE 20

Single-layer OLED devices were made with dendrimer 33 using the procedure described in Example 16, except that at step 5 the oxygen plasma treatment was for 4 minutes at 70 W. The concentration of the solution for spin-coating was 20 mg/ml of 33 in CHCl$_3$ and it was spun at 1800 rpm for 60 sec. The device structure was ITO/33/Ca (20 nm)/Al (60 nm).

Figure 8:
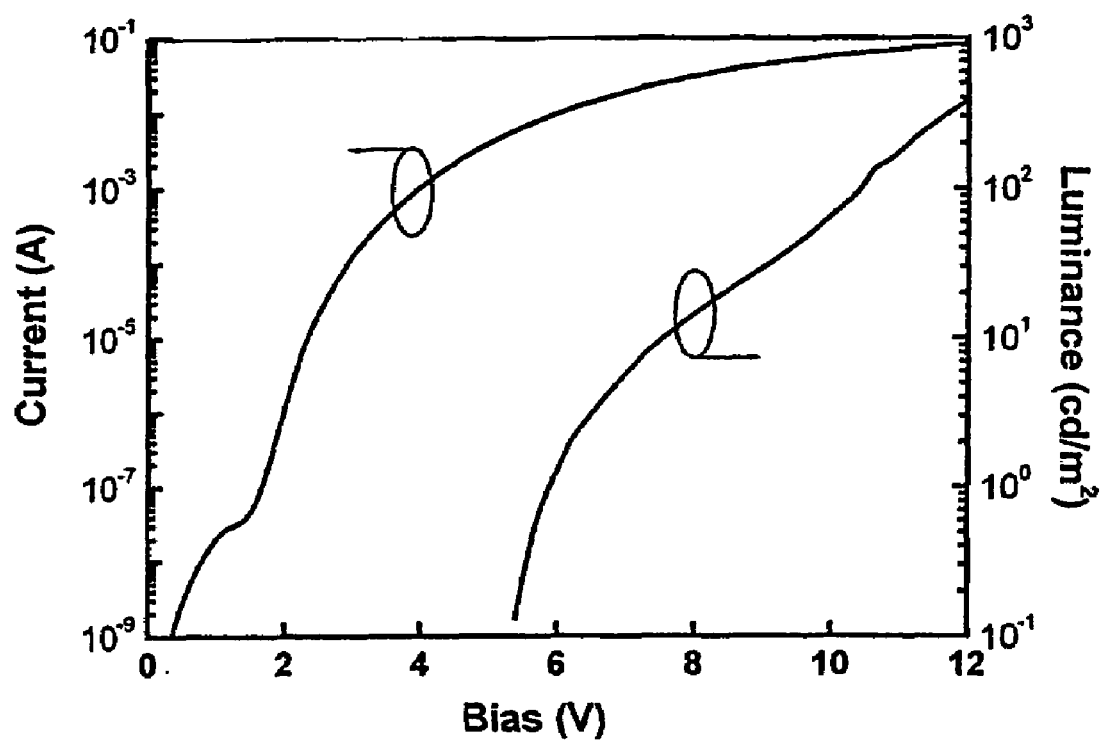
FIG. 8 shows the current-voltage and luminance-voltage characteristics of a device containing a second generation iridium dendrimer (Examples 18-20).
Figure 9:
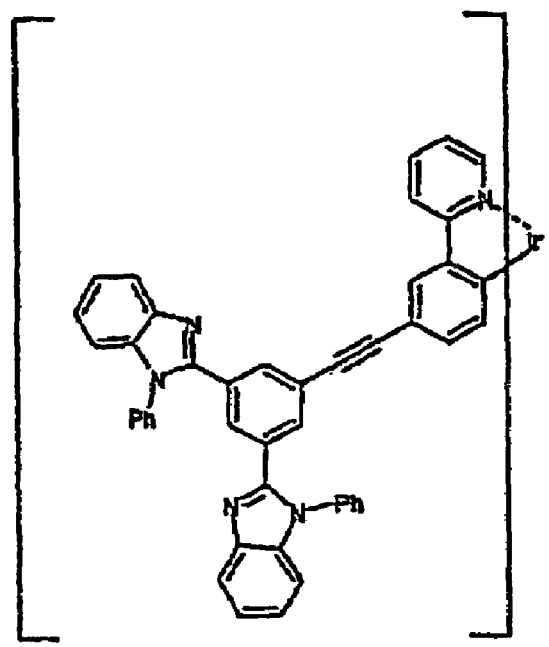
FIG. 9 shows examples of dendrimers with a dendron.
Figure 9:
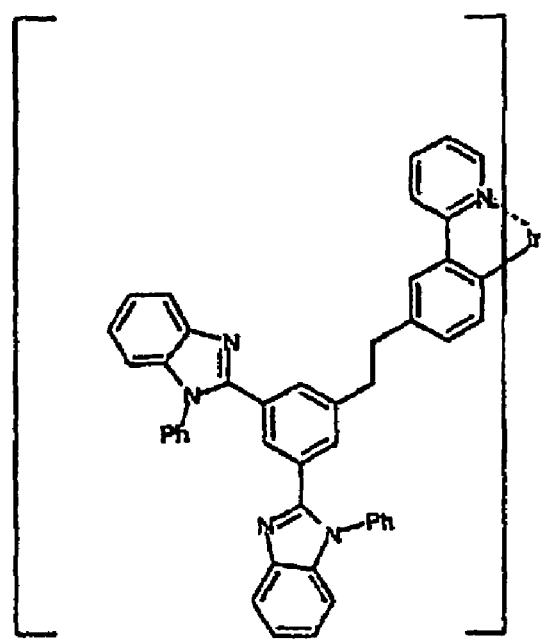

The device passed a relatively large current (see FIG. 8) showing the dendrimer has good charge transporting properties, but in this simple device structure charge recombination was inefficient leading to a relatively low efficiency of 0.01 cd/A at 100 cd/m$^2$ and 10.5 V. The CIE coordinates of the emission are x=0.355, y=0.586.

EXAMPLE 21

Bi-layer OLED devices were made with a light emitting layer containing dendrimer 33 and an evaporated electron transporting layer of 2,2',2"-(1,3,5-phenylene)tris[1-phenyl-1H-benzimidazolyl) (TPBI). The devices were fabricated following the method described in example 16, except that the oxygen plasma treatment was for 4 min at 70 watts, and there was the additional step of vacuum depositing a layer of TPBI prior to deposition of the cathode layers. The concentration of the solutions of light emitting material was 10 mg/ml in CHCl$_3$ and the spin speed was 2300 rpm for 60 sec. The structures of the two types of devices are shown below in which 33 was used as a neat layer, and 33 was blended with 4,4'-N,N'-dicarbazole-biphenyl (CBP), respectively.

ITO/33/TPBI/LiF/Ca/Al
ITO/33:CBP (20:80 weight %)/TPBI/Li/Ca/Al

CIE co-ordinates for the neat device were x=0.342, y=0.614, and for the CBP blend device were x=0.348, y=0.608.

The peak efficiency was 0.4 cd/A at 6 V and ~1000 cd/m$^2$ for the neat bi-layer device. The peak efficiency was 9 cd/A at 7.9 V and ~7000 cd/m$^2$ for the 33:CBP blended bi-layer device. Neither of these device structures had been optimised for efficiency.

At a given voltage there is a higher current passing through the device in which 33 is a neat material, then in the device in which 33 is blended with CBP, confirming the charge-transporting properties of 33.

The invention claimed is:

1. A phosphorescent organometallic dendrimer with a metal cation and two or more coordinating groups as part of its core and wherein at least two of said coordinating groups each have a dendron attached, at least one of which dendron comprises at least one nitrogen atom which forms part of an aromatic ring system or is directly bonded to at least two aromatic groups, and wherein the dendrons comprise branching units selected from unfused and fused aryl and heteroaryl groups and nitrogen atoms.

2. A phosphorescent organometallic dendrimer according to claim 1 wherein at least one dendron comprises at least one nitrogen atom which forms part of an aromatic ring.

3. A phosphorescent organometallic dendrimer according to claim 1 wherein at least one dendron comprises at least one nitrogen atom directly attached to 2 or 3 aryl or heteroaryl groups.

4. A phosphorescent organometallic dendrimer according to claim 1, wherein at least one dendron comprises at least one nitrogen atom which forms part of an aromatic ring and further comprises at least one nitrogen atom which is directly attached to 2 or 3 aryl or heteroaryl groups.

5. A phosphorescent organometallic dendrimer according to claim 1, which is phosphorescent in the solid state.

6. A phosphorescent organometallic dendrimer according to claim 1 which has at least one at least partly conjugated dendron.

7. A phosphorescent organometallic dendrimer according to claim 2 wherein at least one dendron comprises at least one nitrogen atom which forms part of a carbazole ring.

8. A phosphorescent organometallic dendrimer according to claim 1 wherein the dendrimer comprises 3 to 21 carbazole units.

9. A phosphorescent organometallic dendrimer according to claim 1 which has the formula (I):—

CORE-[DENDRON]$_n$     (I)

in which CORE represents a group containing a metal cation, n represents an integer of 2 or more, each DENDRONs represents a dendritic molecular structure comprising at least one nitrogen atom which forms part of an aromatic ring system or is directly attached to at least two aromatic groups, such that two or more coordinating groups have different DENDRONs attached, CORE terminating in the single bond to the first nitrogen atom or aromatic ring to which more than one dendritic chain is attached, said nitrogen atom or ring forming part of said DENDRON.

10. A phosphorescent organometallic dendrimer according to claim 9 wherein CORE terminates in a single bond to a first nitrogen atom which forms part of an aromatic ring system to which more than one dendritic chain is attached.

11. A phosphorescent organometallic dendrimer according to claim 9, wherein at least one said DENDRON comprises an aromatic group in conjugation with a said nitrogen atom or a nitrogen-containing aromatic ring system.

12. A phosphorescent organometallic dendrimer according to claim 9 wherein the said single bond is attached to a carbazole group to which more than one dendritic chain is attached.

13. A phosphorescent organometallic dendrimer according to claim 9 wherein the said single bond is attached to an aryl group to which one or more carbazole groups are attached.

14. A phosphorescent organometallic dendrimer according to claim 1 which has the formula (I):—

CORE-[DENDRON]$_n$ (I)

in which CORE represents a group containing a metal cation, n represents an integer of 2 or more, each DENDRON represents a dendritic molecular structure comprising at least one nitrogen atom which forms part of an aromatic ring system or is directly attached to at least two aromatic groups, such that two or more coordinating groups have different DENDRONs attached, CORE terminating in the single bond to the first sp$^2$ hybridised carbon atom to which more than one dendritic chain is attached.

15. A phosphorescent organometallic dendrimer according to claim 1 wherein the links between branching groups in the dendron are phenyl or fluorenyl groups.

16. A phosphorescent organometallic dendrimer according to claim 1 wherein the CORE is represented by formula (II):—

M[X—]$_q$Y$_r$ (II)

where M is a metal ion, each [X—], which are the same or different, is a coordinating group X attached to a single bond in which CORE terminates, each Y, which may be the same or different, is a coordinating group, q is an integer of 2 or more and r is 0 or an integer, the sum of (a·q)+(b·r) being equal to the number of coordination sites available on M, wherein a is the number of coordination sites on [X—] and b is the number of coordination sites on Y.

17. A phosphorescent organometallic dendrimer according to claim 1, wherein at least one surface group is attached to the distal end of the dendrites.

18. A phosphorescent organometallic dendrimer according to claim 17 wherein the surface group is such as to allow solution processing.

19. A phosphorescent organometallic dendrimer according to claim 17 wherein at least one surface group is selected from a further-reactable alkene, (meth)acrylate, sulphur-containing, or silicon-containing group; sulphonyl group; polyether group; C$_1$-to-C$_{15}$ alkyl group; amine group; mono-, di or tri-C$_1$-to-C$_{15}$ alkyl amine group; —COOR group wherein R is hydrogen or C$_1$-to-C$_{15}$ alkyl; —OR group where R is hydrogen, aryl, or C$_1$-to-C$_{15}$ alkyl or alkenyl; —O$_2$SR group wherein R is C$_1$-to-C$_{15}$ alkyl or alkenyl; —SR group wherein R is aryl, or C$_1$-to-C$_{15}$ alkyl or alkenyl; —SiR$_3$ group wherein the R groups are the same or different and are hydrogen, C$_1$-to-C$_{15}$ alkyl or alkenyl, or —SR' group (R' is aryl or C$_1$-to-C$_{15}$ alkyl or alkenyl), aryl, or heteroaryl.

20. A phosphorescent organometallic dendrimer according to claim 19 wherein the surface is such as to allow patterning.

21. A light emitting device which comprises at least one layer that contains a phosphorescent organometallic dendrimer with a metal cation and two or more coordinating groups as part of its core and wherein at least two of said coordinating groups each have a dendron attached, at least one of which dendrons comprises at least one nitrogen atom which forms part of an aromatic ring system or is directly bonded to at least two aromatic groups, and wherein the dendrons comprise branching units selected from unfused and fused aryl and heteroaryl groups and nitrogen atoms.

22. A device according to claim 21 wherein the dendrimer is the light emitting material.

23. A device according to claim 21 wherein the dendrimer is blended with one or more other dendrimers and/or polymers and/or molecular materials.

24. A device according to claim 21 wherein the layer containing the organometallic dendrimer has been deposited by solution processing.

25. A device according to claim 21 which comprises in addition to the light emitting layer at least one charge transporting and/or injecting layer.

26. A device according to claim 21 which is a light-emitting diode.

27. A photovoltaic device which comprises at least one layer that contains a phosphorescent organometallic dendrimer with a metal cation and two or more coordinating groups as part of its core and wherein at least two of said coordinating groups each have a dendron attached, at least one of which dendrons comprises at least one nitrogen atom which forms part of an aromatic ring system or is directly bonded to at least two aromatic groups, wherein said at least one layer is as defined in claim 1.

28. A process for producing a dendrimer as claimed in claim 1 which process comprises:
(a) providing a core by forming a complex between a metal cation and two or more coordinating groups, at least two of the said groups bearing a reactive functionality; and
(b) treating the core thus provided with two or more dendrons which have been functionalised to render them reactive towards the reactive functionalities present in the core, at least one of the dendrons comprising at least one nitrogen atom which forms part of an aromatic ring system or is directly bonded to at least two aromatic groups.

29. A process according to claim 28 wherein at least one of the coordinating groups does not contain a reactive functionality and consequently remains free of attachment to a dendron in step (b).

30. A process according to claim 28 wherein the core provided in step (a) is represented by formula (II):—

M[X—]$_q$Y$_r$ (II)

in which M is a metal ion, each [X—], which are the same or different, is a coordinating group X attached to a single bond in which CORE terminates, each Y, which may be the same or different, is a coordinating group, q is an integer of 2 or more, and r is 0 or an integer, the sum of (a·q)+(b·r) being equal to the number of coordination sites available on M, wherein a is the number of coordination sites of [X—] and b is the number of coordination sites on Y, and wherein each [X—] includes a reactive functionality.

31. A process for producing a dendrimer as claimed in claim 1 which process comprises:

(a) attaching a coordinating group to each of two or more dendrons, at least one of which comprises at least one nitrogen atom which forms part of an aromatic ring system or is directly bonded to at least two aromatic groups and (b) forming a complex between the coordinating groups and a metal cation which is optionally bonded to one or more ligands which remain in the resulting complex.

* * * * *

UNITED STATES PATENT AND TRADEMARK OFFICE
CERTIFICATE OF CORRECTION

PATENT NO. : 7,641,986 B2
APPLICATION NO. : 10/508061
DATED : January 5, 2010
INVENTOR(S) : Lo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1113 days.

Signed and Sealed this

Sixteenth Day of November, 2010

David J. Kappos
*Director of the United States Patent and Trademark Office*